(12) United States Patent
Reynolds et al.

(10) Patent No.: US 7,860,728 B2
(45) Date of Patent: Dec. 28, 2010

(54) SYSTEM, METHOD, AND COMPUTER PROGRAM PRODUCT FOR REDUCING THE BURDEN ON SCHEDULING SYSTEMS BY FORECASTING A DEMAND FOR MEDICAL RESOURCES USING RETRIEVED BILLING DATA

(75) Inventors: David Reynolds, Hermitage, TN (US); Prakash Raghothamachar, Nashville, TN (US); Mark Soileau, Nashville, TN (US); Eric Vickery, Irondale, AL (US); Milan Zimmermann, Oakville (CA)

(73) Assignee: Syus, LLC, Nashville, TN (US)

( * ) Notice: Subject to any disclaimer, the term of this patent is extended or adjusted under 35 U.S.C. 154(b) by 1264 days.

(21) Appl. No.: 11/351,353

(22) Filed: Feb. 9, 2006

(65) Prior Publication Data
US 2007/0185731 A1     Aug. 9, 2007

(51) Int. Cl.
G06Q 10/00     (2006.01)
G06Q 50/00     (2006.01)
(52) U.S. Cl. .................................. 705/2; 705/3; 705/4
(58) Field of Classification Search .................. 705/2–4
See application file for complete search history.

(56) References Cited

U.S. PATENT DOCUMENTS

| | | | |
|---|---|---|---|
| 6,058,370 A | 5/2000 | Church et al. | |
| 6,314,556 B1 | 11/2001 | DeBusk et al. | |
| 7,222,079 B1 * | 5/2007 | Seare et al. | 705/3 |
| 2002/0120469 A1 * | 8/2002 | Javitt | 705/2 |
| 2003/0097185 A1 | 5/2003 | Goetzke et al. | |
| 2005/0273360 A1 | 12/2005 | Drucker et al. | |

OTHER PUBLICATIONS

International Search Report, dated Jul. 5, 2007.

* cited by examiner

*Primary Examiner*—Gerald J. O'Connor
*Assistant Examiner*—Hiep V. Nguyen
(74) *Attorney, Agent, or Firm*—Moore & Van Allen PLLC; W. Kevin Ransom

(57) ABSTRACT

The present invention generates a forecast factor indicating an anticipated demand for a medical resource in a medical facility during a selected time period. The invention generates the forecast factor using billing data retrieved from one or more billing data systems wherein the retrieved billing data is from a prior time period that is comparable to the selected time period. The invention may also generate a schedule of the medical resource using the determined forecast factor such that the generated schedule may substantially correspond to the anticipated demand for the medical resource during the selected time period. In addition, the invention may also generate one or more displays of the determined forecast factor to a user and may also receive a user input for selecting and/or modifying the protocol used to determine the forecast factor.

43 Claims, 12 Drawing Sheets

SYSTEM, METHOD, AND COMPUTER PROGRAM PRODUCT FOR REDUCING THE BURDEN ON SCHEDULING SYSTEMS BY FORECASTING A DEMAND FOR MEDICAL RESOURCES USING RETRIEVED BILLING DATA

BACKGROUND OF THE INVENTION

1. Field of the Invention

The present invention relates to the field of medical resource utilization including, but not limited to the scheduling of medical staff and medical facilities. More particularly, embodiments of the present invention collect and compile billing data from one or more medical billing systems and convert the billing data into historical demand information for a medical resource so as to generate a forecasted demand for the medical resource within a medical facility during a selected time period.

2. Description of Related Art

The scheduling of medical personnel, including clinicians, technicians, and other staff, and other medical resources, such as procedure rooms, is becoming increasingly complex as medical facilities grow larger and as multiple medical facilities and campuses become consolidated under a single administrative and/or ownership entity such as a health care corporation. However, in conventional health care administration systems, the scheduling of specific personnel and medical procedure space within a medical facility is largely determined by estimations based on maximum potential demand for a given resource during a selected time period.

For example, in an anesthesiology department having a number of available procedure rooms, a typical weekday may have a peak demand for procedure rooms and clinicians (which is often determined by a number of procedures (i.e. administrations of anesthesia) during a given two-hour span in the middle of the day. In conventional scheduling methods, scheduling administrators often schedule sufficient medical personnel (including anesthesiologists and certified nurse anesthetists, for example) and procedure rooms to accommodate the peak number of concurrent procedures for an entire shift (i.e. a 10-hour shift from 0700-1700), where the peak number of concurrent procedures may be occurring only during a 2 hour span in the middle of the day.

However, conventional scheduling systems and techniques do not utilize concurrent activities information (such as information on a number of concurrent medical procedures during a given time period gleaned from billing data generated in a selected medical facility) that may inform a scheduling administrator of the time period in which peak demand for one or more medical resources is expected to be experienced.

Furthermore, conventional scheduling systems are not configured to distill concurrent activities information from billing data taken from one or more medical billing data systems, which may provide billing data that may be used (if properly manipulated and/or interpreted) to aid in the prediction of demand patterns for a medical resource within a medical facility during a selected time period. For example, medical billing systems often contain detailed information regarding the type of procedure performed and the clinicians and/or staff members required to perform a specific procedure. Billing data may also include time stamp information and/or duration information that may be indicative of the time required to perform a given procedure and/or the time spent by various clinicians and/or staff members to perform a given role in a medical procedure. Billing data tied to particular medical procedures may also provide a more realistic historical profile of demand for medical resources (such as medical personnel and/or medical facility space) than, for example, the historical usage of medical supplies and/or other inventory items. This may be especially true for medical procedures such as anesthesia administration, which may utilize relatively few inventoried medical disposables, but may require significant medical resources including, for example, facility space for patient preparation and patient recovery and clinicians to oversee patient preparation, administration of anesthesia, and patient recovery.

While billing data may provide a large amount of data that is generally indicative of demand for a given medical resource in a medical facility during a selected time period, such billing data is often non-standardized across medical facilities and/or across administrative entities. For example, some billing data may only include a time stamp and a procedure code indicative of a specific service performed in a medical procedure. For example, in the billing of a particular administration of anesthesia, the billing data may indicate the service codes including, but not limited to: patient preparation, anesthesia administration, surgery and/or medical procedure, and patient recovery. Even if these service codes are accompanied by a time stamp as part of a billing data set, the billing data set may not be immediately useful to a scheduling administrator, because such codes do not immediately indicate the types of personnel, the expected duration, and/or the type of procedure room required for each service. Thus, it may be necessary, in some cases, to interpret and/or convert billing data into alternative data types that may be predictive of the utilization of particular medical resources during a selected time period in order to aid a scheduling administrator in meeting a predicted demand during a future comparable time period.

Thus limitations in current scheduling systems and limitations inherent in billing data, that may otherwise aid scheduling administrators in generating more efficient schedules, may create a burden on scheduling administration systems as well as create inefficiencies that may exacerbate the already high costs of health care. Specifically, since conventional scheduling systems are not capable of retrieving billing information from a medical billing system and converting such billing information into usable scheduling data, such scheduling systems are incapable of ascertaining an accurate history of the actual demand for specific medical resources (such as procedure rooms and/or medical personnel) during a selected time period that may be predictive of demand for such resources in a comparable subsequent time period. In order to ensure that sufficient medical resources may be on hand in a given medical facility during a selected time period, scheduling administrators may be required to over-schedule personnel and facilities space to accommodate the busiest portions of a particular time period. For example, a scheduling administrator may be required to schedule sufficient medical personnel and facility space to accommodate 5 substantially concurrent medical procedures in a particular medical facility for an entire shift even though the actual demand for such medical resources may only exist (as indicated by billing data, for example) during a comparatively short time window during the middle of the shift. Conventional search systems lack the capability of accessing billing data for a selected time period, much less translating and/or converting such billing data into predictive forecast data that may be either presented to a user prior to the scheduling of medical resources for a subsequent comparable time period. Thus, some users (such as scheduling administrators and/or physicians) will be required to rely on gross estimates ascertained from "worst-case" maximum demand scenarios. Thus, conventional scheduling systems may over-schedule medical resources for the majority of a shift (or other time period) in order to ensure that sufficient resources are available in a medical facility during a particular time period.

Therefore, there exists a need for an improved system to solve the technical problems outlined above that are associated with conventional medical resource scheduling systems. More particularly, there exists a need for a system capable of converting medical billing data that may be retrieved from a medical billing system into a format that may be indicative of a historical demand for a medical resource in a particular medical facility during a selected time period. There also exists a need for a system capable of providing scheduling forecast information to a scheduling administrator (via a display, for example) such that the administrator may effectively use the converted billing data in order to generate a schedule of medical resources that is optimally matched to a predicted demand for medical resources during a selected time period. In addition, there exists a need for a system that may export a forecasted demand for medical resources (as a forecast schedule, for example) into a scheduling system and/or calendar such that the forecast schedule shown in the calendar is optimized for efficiency based at least partially upon the forecasted demand for medical resources (such as medical personnel and/or medical procedure rooms).

BRIEF SUMMARY OF THE INVENTION

The needs outlined above are met by the present invention which, in various embodiments, provides system, method, and computer program product embodiments that overcome many of the technical problems discussed above, as well other technical problems, with regard to the scheduling of medical resources in a medical facility. Specifically, in one embodiment, a system for optimizing a schedule of at least one medical resource in at least one medical facility using a billing data set is provided. According to some embodiments, the system comprises a medical billing system comprising the billing data corresponding to at least one medical procedure being performed using the at least one medical resource in the at least one medical facility during a first time period. The data within the billing data may be indicative of a utilization of the at least one medical resource during the first time period. The system may further comprise a forecasting module in communication with said medical billing system, wherein the forecasting module may retrieve the billing data set from the medical billing system. Furthermore, the forecasting module may also convert data within the billing data set into a utilization data set corresponding to a historical demand for the medical resource in the medical facility during the first time period. In addition, the forecasting module may also determine a forecast factor using data within the billing data set, wherein the forecast factor corresponds, for example, to an expected demand for the medical resource in the medical facility during a second time period (subsequent to the first time period) such that the at least one medical resource is efficiently utilized during the second time period. According to various embodiments, the medical resource for which the expected demand may be determined may include, but is not limited to: a clinician and a medical procedure room within the at least one medical facility.

In some system embodiments, the forecasting module may further generate the schedule of the medical resource such that the schedule corresponds to the determined forecast factor during the second time period. Furthermore, the forecasting module may also be configured to transfer the generated schedule to a scheduling calendar. In some system embodiments, the forecasting module may also comprise a memory device for storing the retrieved billing data set and/or a user interface for displaying the forecast factor to a user. In some such embodiments, the forecast module may displays the forecast factor to the user via the user interface in a display that may include, but is not limited to: a chart of substantially concurrent medical procedures in the at least one medical facility during the first time period; a chart of a quantity of the at least one medical procedure in the at least one medical facility during the first time period; a Gantt chart of the at least one medical procedure during the first time period; and combinations thereof.

According to various system embodiments, the data within the billing data set may include, but is not limited to: an identification code for identifying a type of the at least one medical procedure; a time of the at least one medical procedure; a duration of the at least one medical procedure; a location of the at least one medical facility; a personnel identification code for identifying a clinician performing the at least one medical procedure; and combinations thereof. Using such billing data, the system embodiments of the present invention may determine a forecast factor that may include, but is not limited to: a percentage of time the at least one medical facility is in use during the first time period; a number of clinicians required to staff the at least one medical procedure; a qualification of a clinician required to staff the at least one medical procedure; a number of concurrent medical procedures occurring in the at least one medical facility during the first time period; a percentage of time that a selected number of concurrent medical procedures are occurring in the at least one medical facility during the first time period; and combinations thereof. Furthermore, the first and second time periods for which the system embodiments operate may be comparable time periods of substantially equivalent duration including, but not limited to: a day; a week; a month; and a year.

Various system embodiments of the present invention may also comprise a conversion module in communication with the medical billing system and/or the forecasting module. The conversion module may comprise data and corresponding utilization information. According to some such embodiments, the forecasting module may interrogate the conversion module so as to convert the data within the billing data set into a utilization data set comprising the utilization information corresponding to a historical demand for the medical resource in the medical facility during the first time period.

Further, the present invention also provides methods and/or computer program products for optimizing a schedule of at least one medical resource in at least one medical facility using a billing data set from a medical billing system. As described generally above, the billing data set may corresponding to at least one medical procedure being performed using the at least one medical resource in the at least one medical facility during a first time period. Furthermore, the data within the billing data set may be indicative, for example, of a utilization of the at least one medical resource during the first time period. According to one embodiment, the method and/or computer program product may comprise steps for: retrieving the billing data set from the medical billing system; converting data within the billing data set into a utilization data set corresponding to a historical demand for the medical resource in the medical facility during the first time period; and determining a forecast factor using data within the billing data set. The forecast factor determined in some embodiments may correspond, for example, to an expected demand for the medical resource in the medical facility during a second time period (subsequent to the first time period) such that the at least one medical resource is efficiently utilized during the second time period. According to various method and/or computer program products, the first and second time periods may be comparable time periods including, but not limited to: a day; a week; a month; and a year. Furthermore, in various method and/or computer program products, the determined forecast factor may apply to forecast demand for various medical resources including, but not limited to a clinician and a medical procedure room within the at least one medical facility.

Some method and/or computer program embodiments may also comprise steps for redistributing the schedule of the at least one medical resource such that the schedule corresponds to the determined forecast factor during the second time period and/or steps for transferring the generated schedule to a scheduling calendar. Furthermore, some method and/or computer program product embodiments may also comprise displaying the forecast factor to a user (via a user interface, for example). The displaying step may, in some embodiments, comprise displaying the forecast factor in a graphical display that may include, but is not limited to: a chart of substantially concurrent medical procedures in the at least one medical facility during the first time period; a chart of a quantity of the at least one medical procedure in the at least one medical facility during the first time period; and a Gantt chart of the at least one medical procedure during the first time period.

In some method and/or computer program product embodiments the data within the retrieved billing data set may include, but is not limited to: an identification code for identifying a type of the at least one medical procedure; a time of the at least one medical procedure; a duration of the at least one medical procedure; a location of the at least one medical facility; a personnel identification code for identifying a clinician performing the at least one medical procedure; and combinations thereof. Furthermore, the forecast factor generated by the determining step described above may include, but is not limited to: a percentage of time the at least one medical facility is in use during the first time period; a number of clinicians required to staff the at least one medical procedure; a qualification of a clinician required to staff the at least one medical procedure; a number of concurrent medical procedures occurring in the at least one medical facility during the first time period; and a percentage of time that a selected number of concurrent medical procedures are occurring in the at least one medical facility during the first time period.

In addition, some method and/or computer program product embodiments further comprise steps for interrogating a conversion module comprising data and corresponding utilization information so as to convert the data within the billing data set into a utilization data set comprising the utilization information corresponding to a historical demand for the at least one medical resource in the at least one medical facility during the first time period.

Thus the systems, methods, and computer program products for optimizing a schedule of at least one medical resource in at least one medical facility using a billing data set, as described in the embodiments of the present invention, provide many advantages that may include, but are not limited to: retrieving billing data set from a selected time period that may be highly predictive of demand for a particular medical resource during a subsequent comparable time period; converting the retrieved billing data set into usable scheduling information that may be useful to scheduling administrators for optimizing the scheduling of medical resources in one or more medical facilities; providing a clear user-friendly display of a forecasted demand for a particular medical resource in an upcoming time period so as to allow an administrator and/or user to prepare an optimized staffing and/or facilities schedule; and providing forecast factors and/or scheduling predictions or forecasts based on actual billing data that may be easily exported to a scheduling and/or calendar software suite.

These advantages and others that will be evident to those skilled in the art are provided in the system, method, and computer program product of the present invention. Importantly, all of these advantages allow the system to utilize medical billing data to generate scheduling forecast factor that may be presented to a user such that the user is less likely to over-schedule and/or under-schedule medical resources in a manner that may either create resource waste or overburden medical staff or facilities.

BRIEF DESCRIPTION OF THE SEVERAL VIEWS OF THE DRAWINGS

Figure 1:
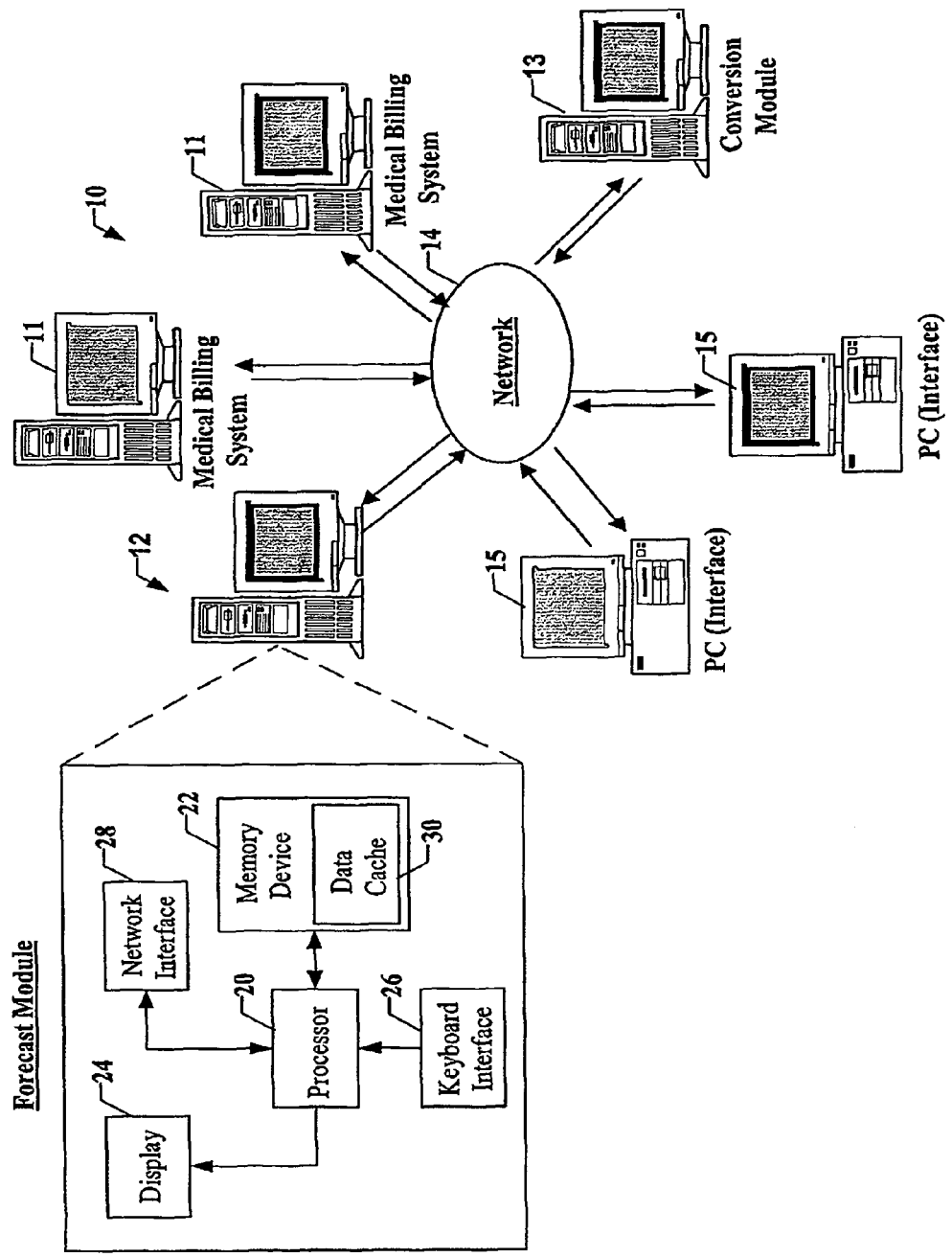

Having thus described the invention in general terms, reference will now be made to the accompanying drawings, which are not necessarily drawn to scale, and wherein:

FIG. 1 illustrates an exemplary network environment in which the systems, methods, and computer program products may be implemented according to one embodiment of the present invention.

Figure 2:
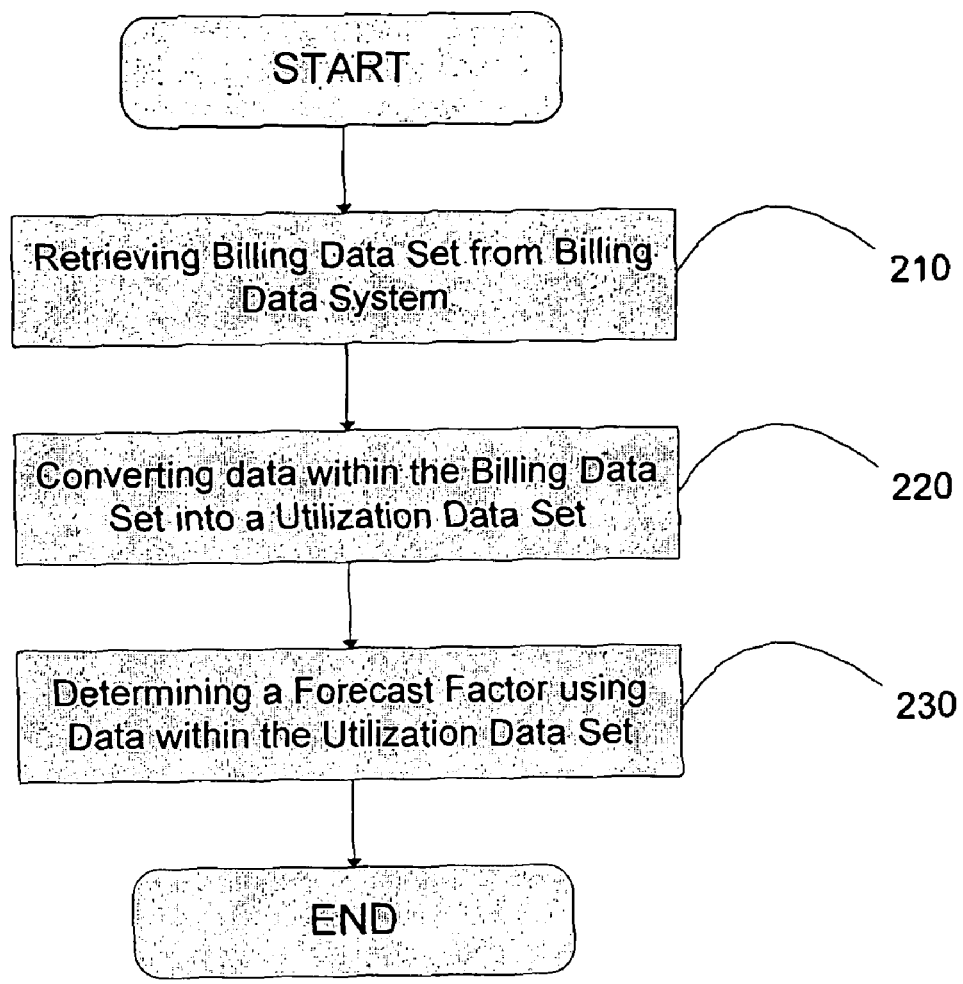

FIG. 2 is an illustration of the operation flow of the systems, methods, and computer program products according to one embodiment of the present invention including retrieving billing data, converting the billing data to usage data, and determining a forecast factor.

Figure 3:
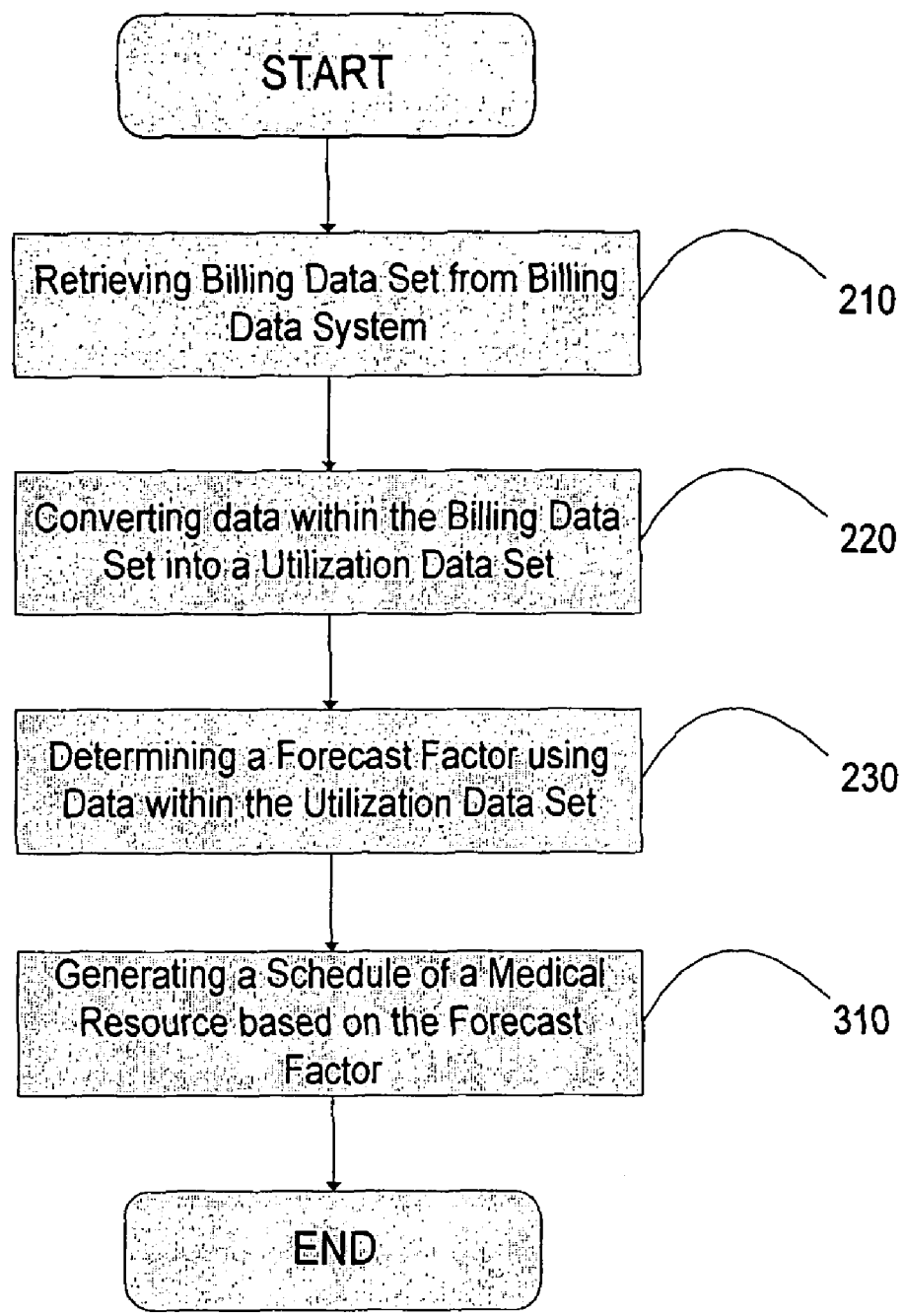

FIG. 3 is an illustration of the operation flow of the systems, methods, and computer program products according to one embodiment of the present invention including retrieving billing data, converting the billing data to usage data, determining a forecast factor, and redistributing a schedule of a medical resource using the forecast factor.

Figure 4:
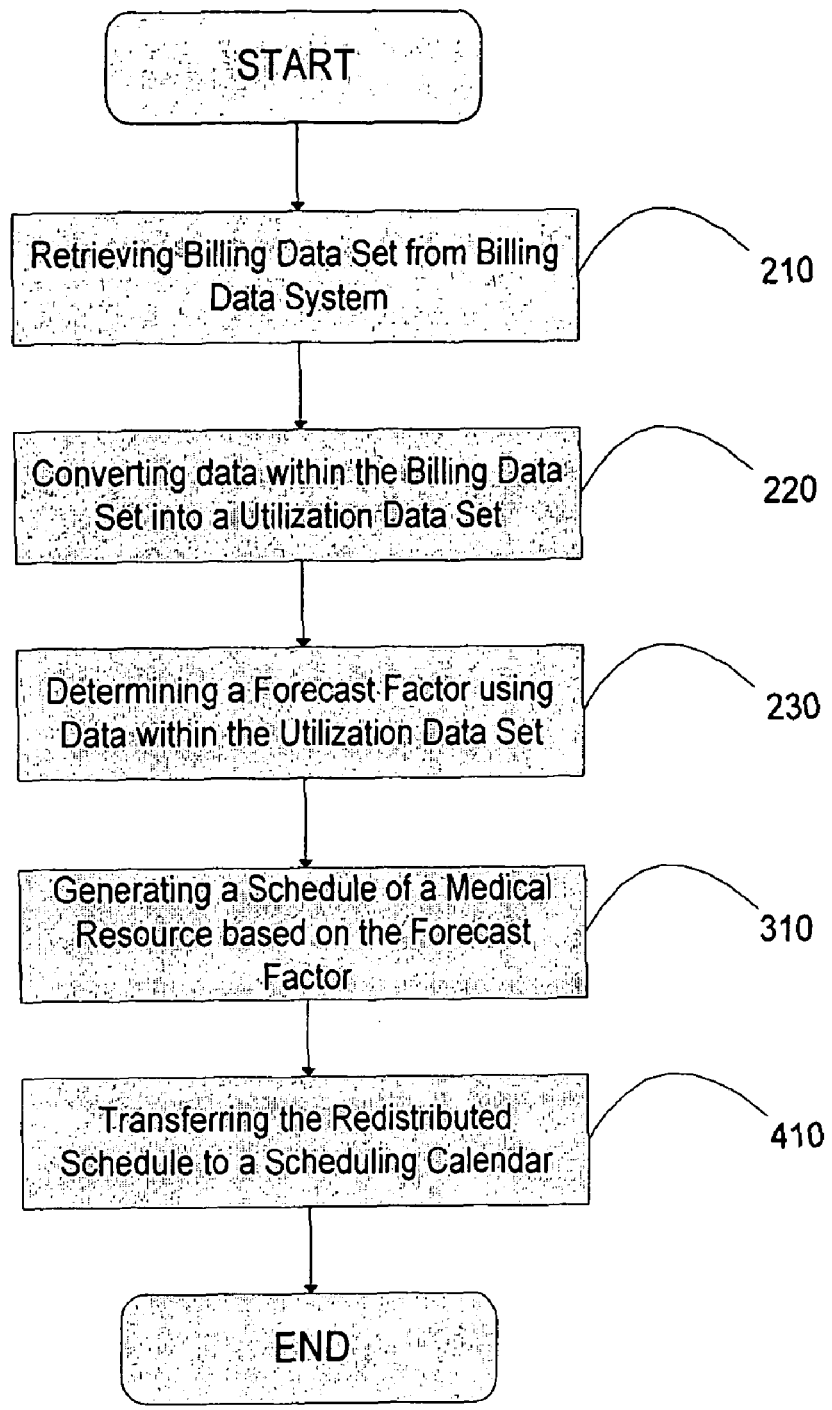

FIG. 4 is an illustration of the operation flow of the systems, methods, and computer program products according to one embodiment of the present invention including retrieving billing data, converting the billing data to usage data, determining a forecast factor, redistributing a schedule of a medical resource using the forecast factor, and transferring the generated schedule to a scheduling calendar.

Figure 5:
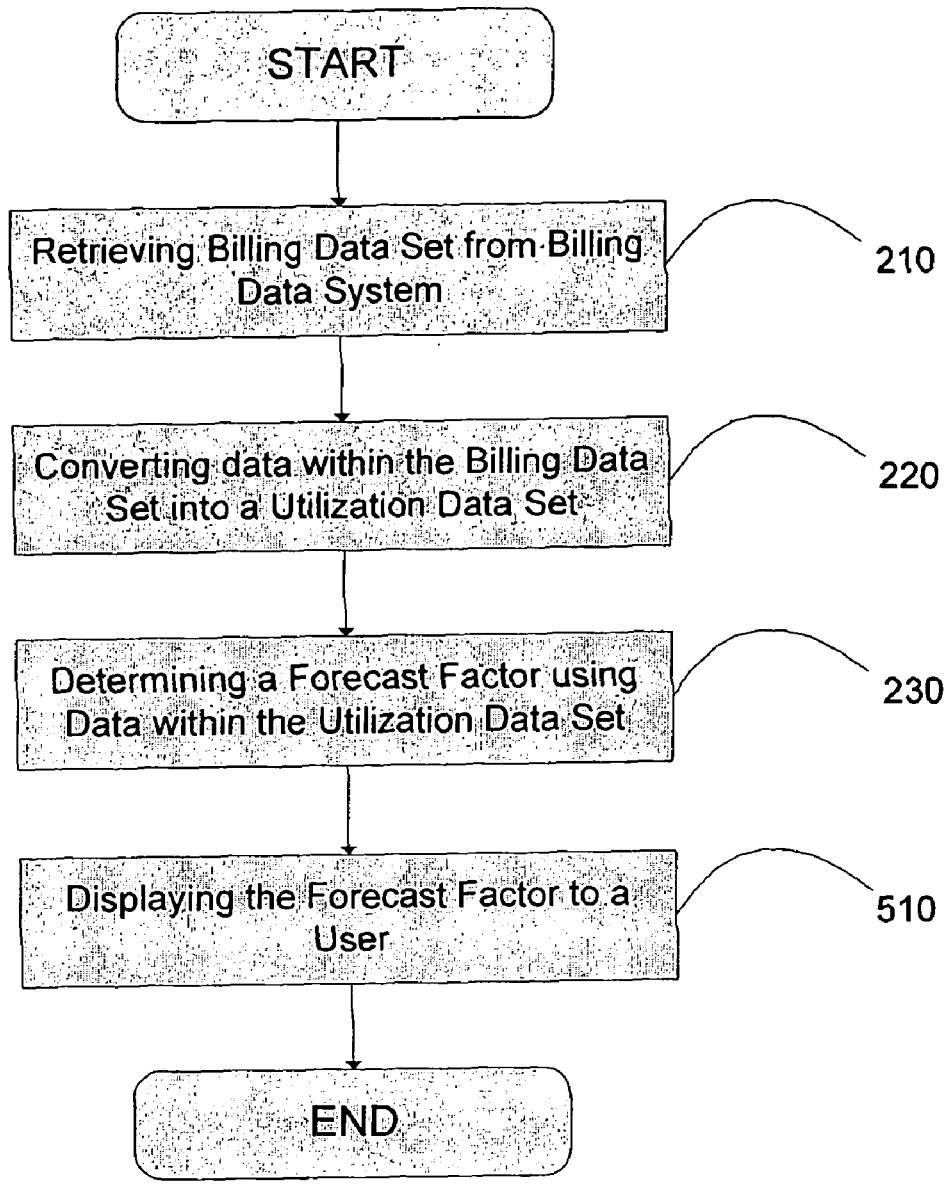

FIG. 5 is an illustration of the operation flow of the systems, methods, and computer program products according to one embodiment of the present invention including retrieving billing data, converting the billing data to usage data, determining a forecast factor, and displaying the forecast factor to a user.

Figure 6:
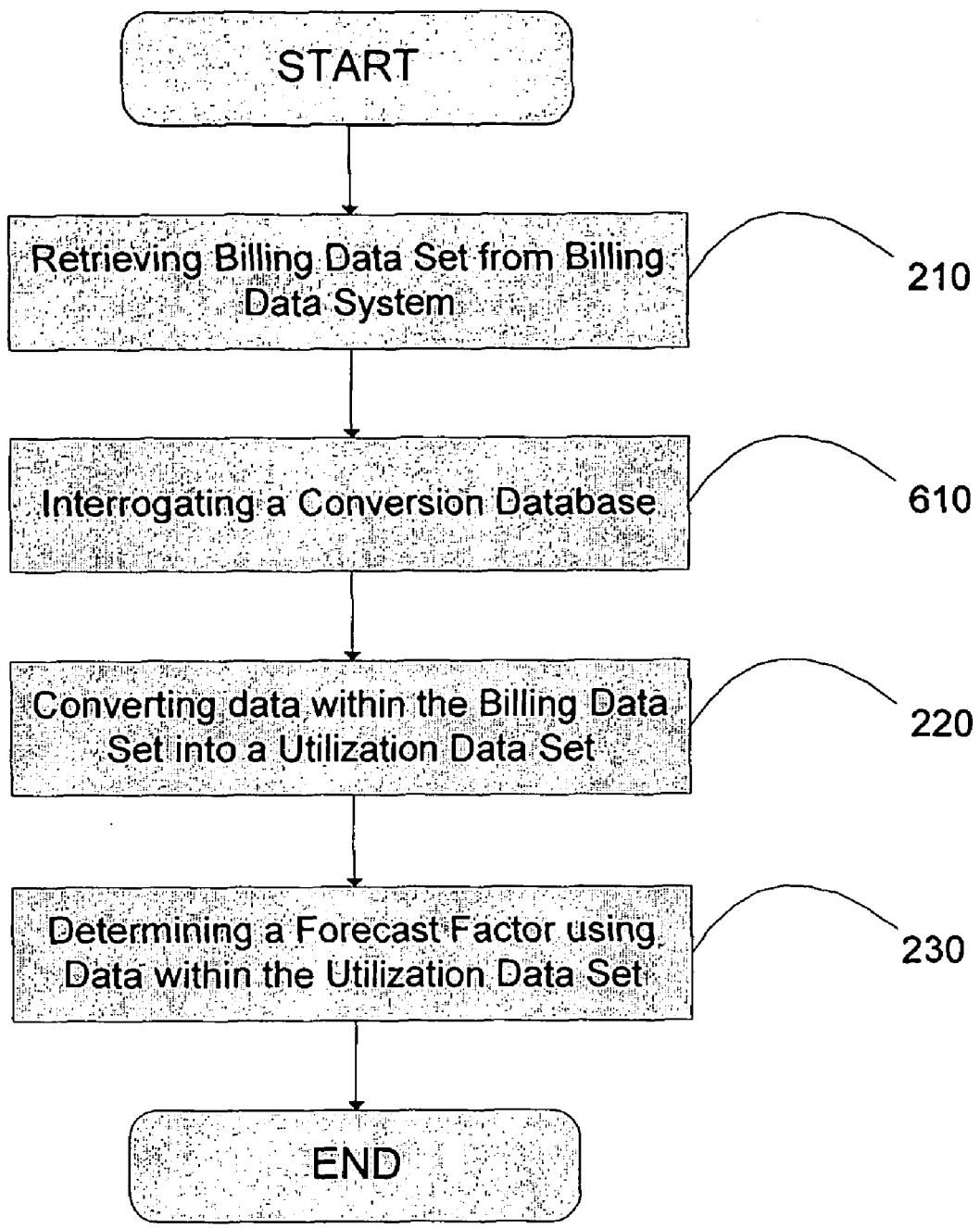

FIG. 6 is an illustration of the operation flow of the systems, methods, and computer program products according to one embodiment of the present invention including retrieving billing data, interrogating a conversion module, converting the billing data to usage data, and determining a forecast factor based on the usage data.

Figure 7:
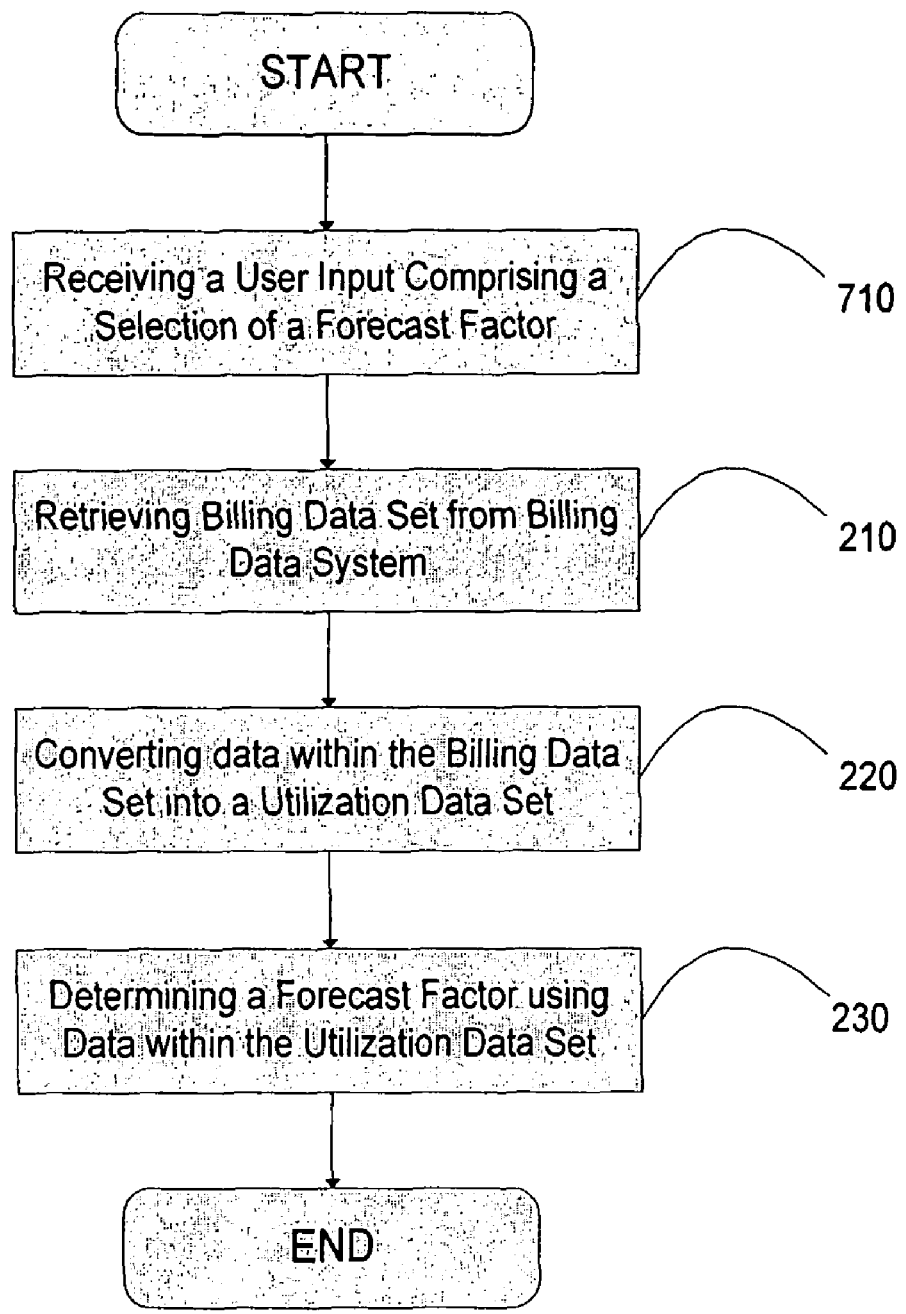

FIG. 7 is an illustration of the operation flow of the systems, methods, and computer program products according to one embodiment of the present invention including receiving a user input, retrieving billing data, converting the billing data to usage data, and determining a forecast factor based on the usage data.

Figure 8:
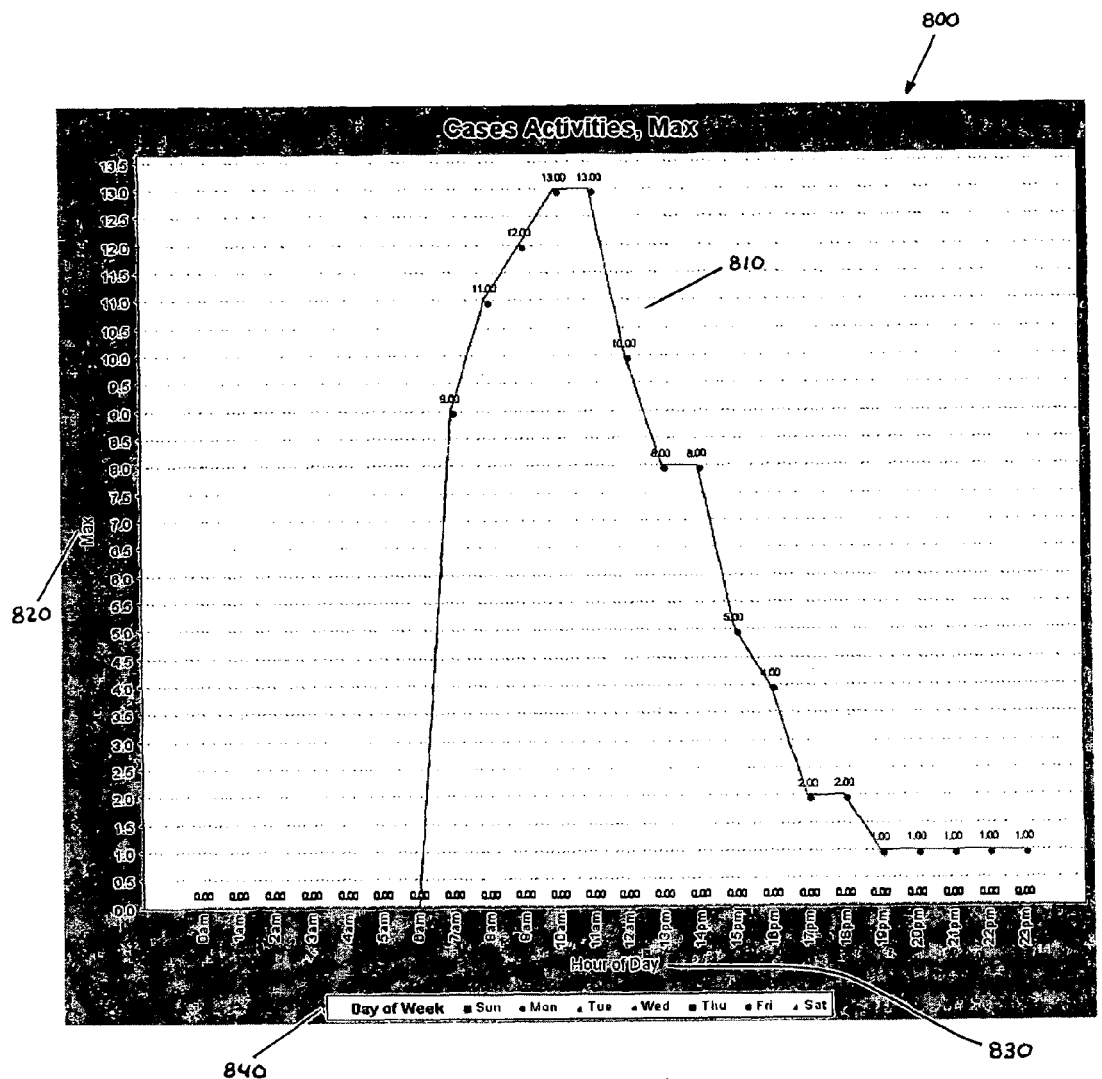

FIG. 8 is a graphical depiction of a display generated according to one embodiment of the systems, methods, and computer program products of the present invention illustrating a forecast factor plot of required medical personnel versus time during a first time period.

Figure 9:
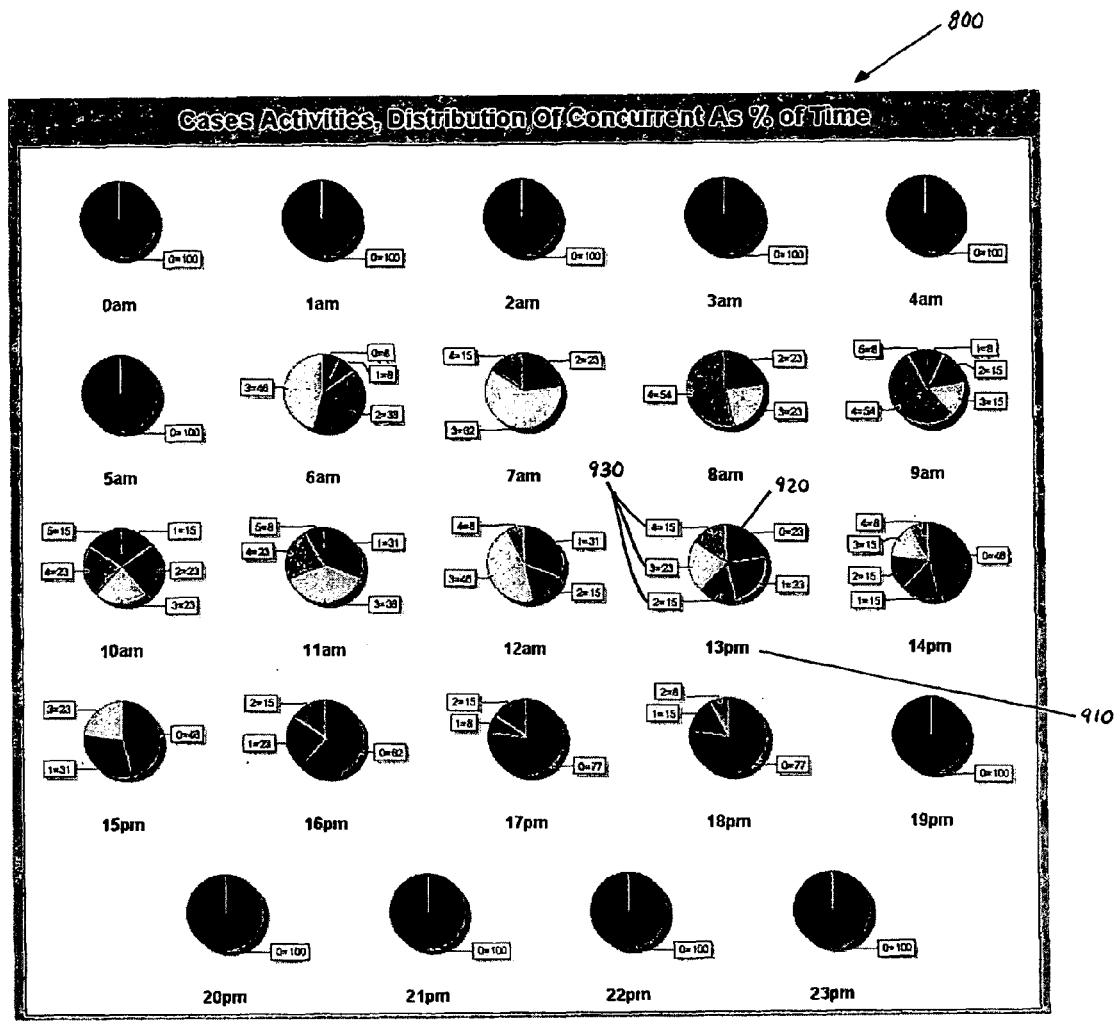

FIG. 9 is a graphical depiction of a display generated according to one embodiment of the systems, methods, and computer program products of the present invention illustrating a forecast factor plot of concurrent medical procedures as a percentage of time during a first time period (a Tuesday, for example).

Figure 10:
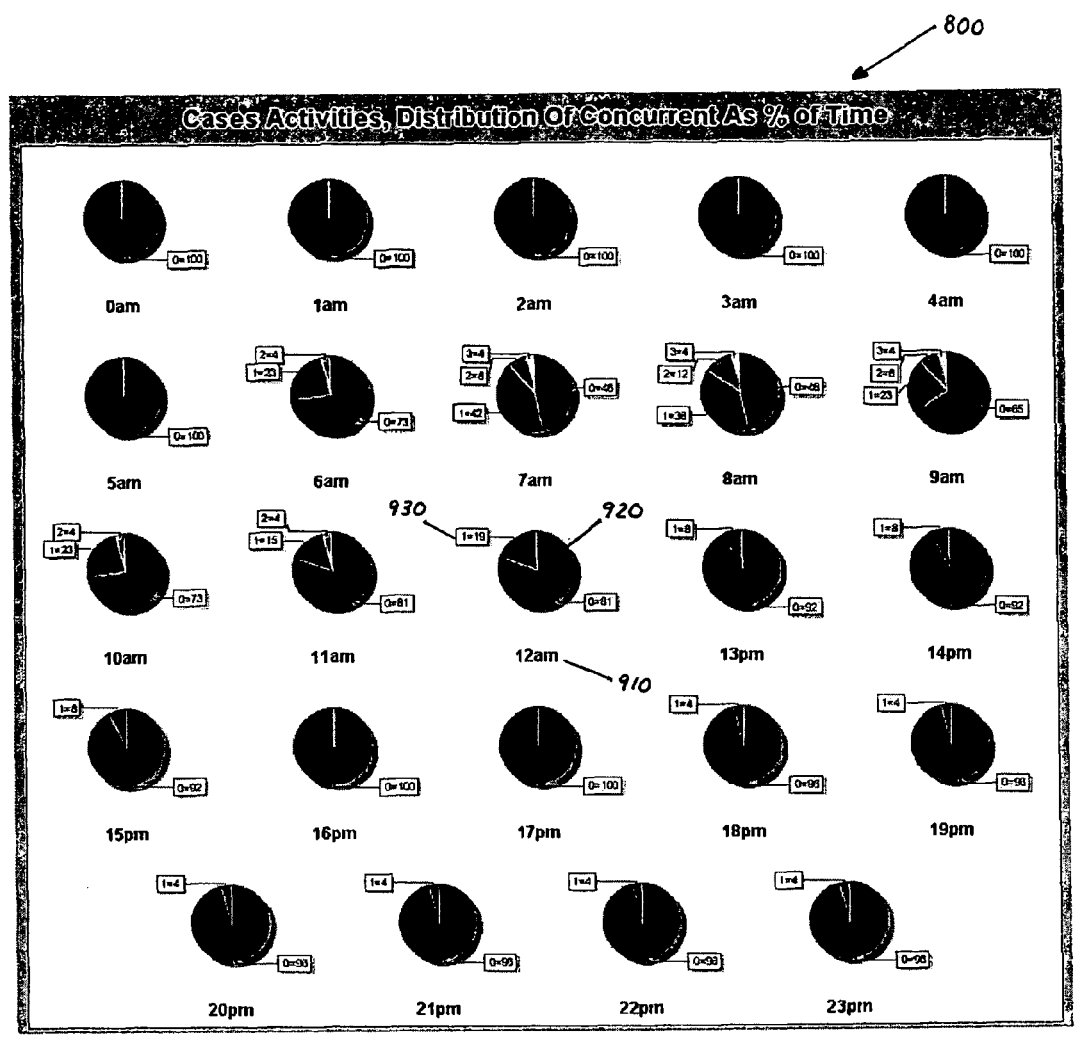

FIG. 10 is a graphical depiction of a display generated according to one embodiment of the systems, methods, and computer program products of the present invention illustrating a forecast factor plot of concurrent medical procedures as a percentage of time during a first time period (a Friday, for example).

Figure 11:
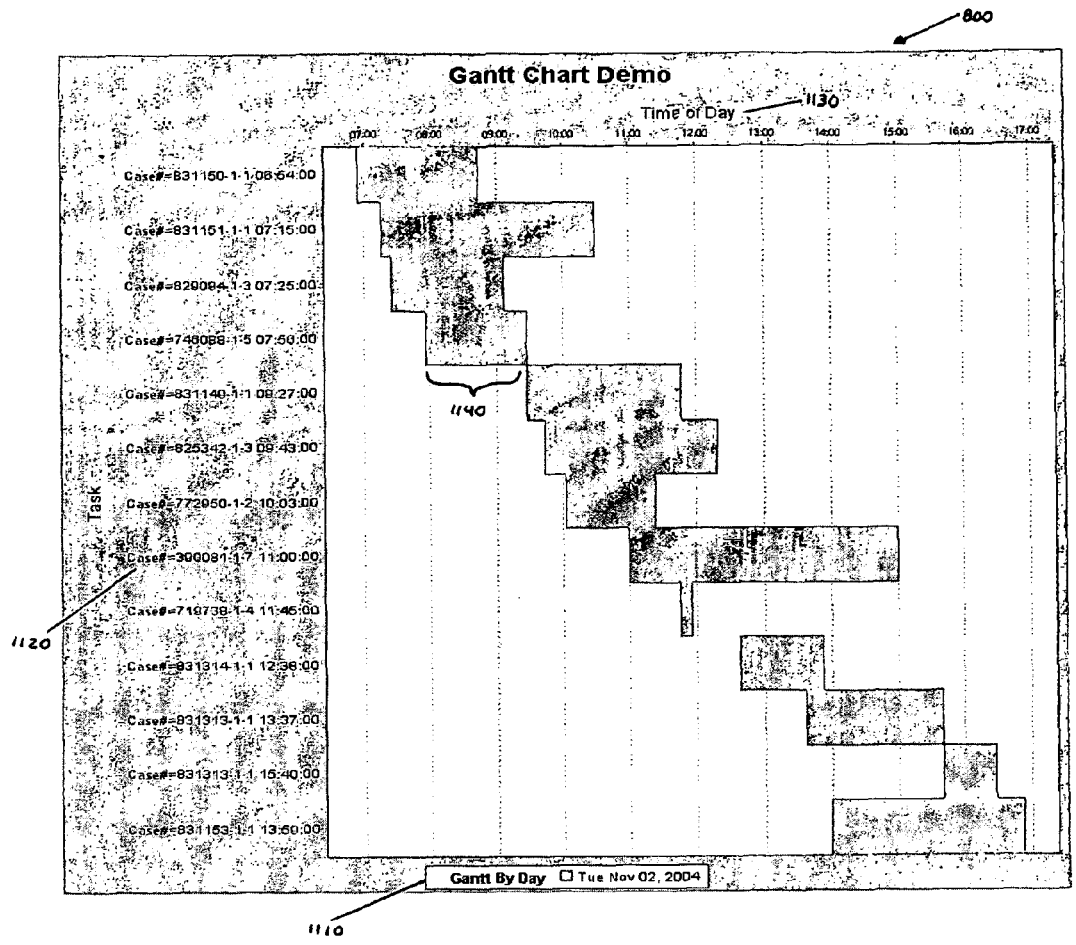

FIG. 11 is a graphical depiction of a Gantt chart display generated according to one embodiment of the systems, methods, and computer program products of the present invention illustrating a forecast factor plot of the start, duration, and end times for at least one medical procedure on a given Tuesday.

Figure 12:
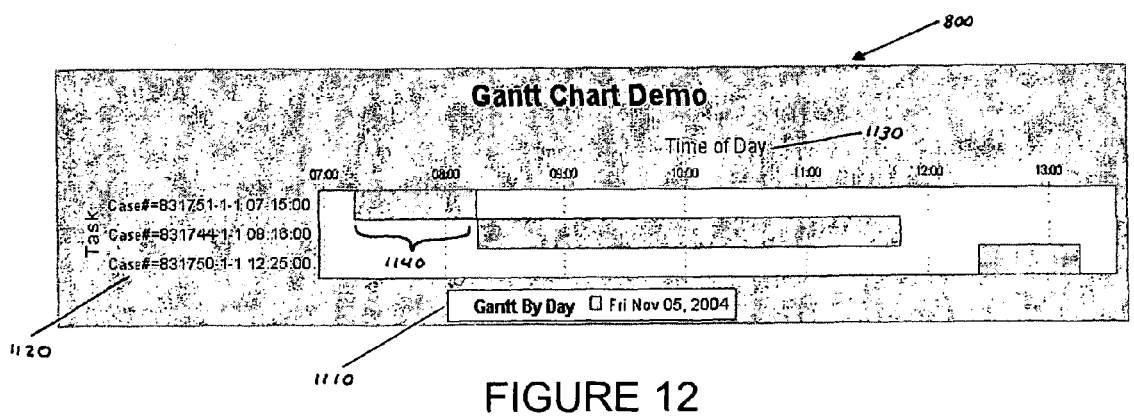

FIG. 12 is a graphical depiction of a Gantt chart display generated according to one embodiment of the systems, methods, and computer program products of the present invention illustrating a forecast factor plot of the start, duration, and end times for at least one medical procedure on a given Friday.

Figure 13:
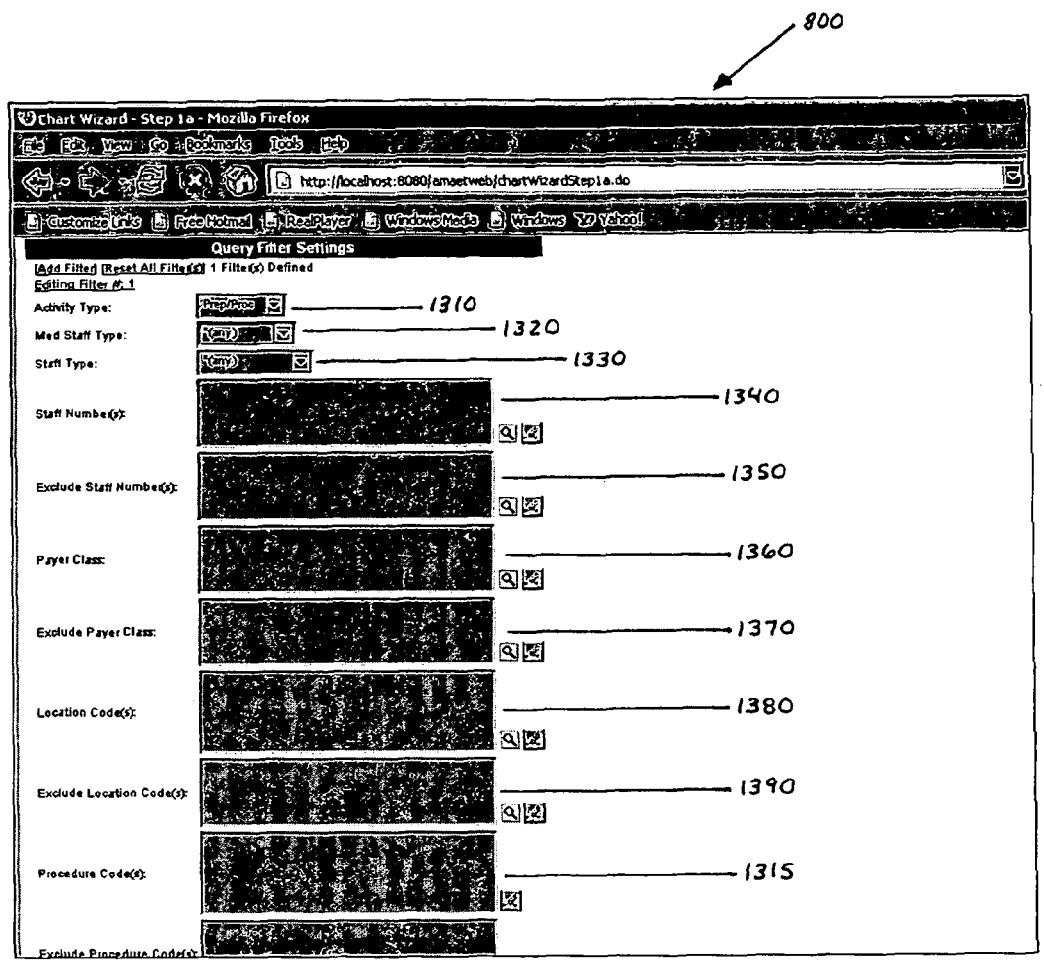

FIG. 13 is a graphical depiction of a user input display generated by a user interface, according to one embodiment of the systems, methods, and computer program products of the present invention, wherein the user input display is configured to receive a user input comprising a selection of a forecast factor.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The various aspects of the present invention mentioned above, as well as many other aspects of the invention are described in greater detail below. The systems, methods, and computer program products of the present invention are described in an anesthesiology medical practice environment. It must be understood that this is only one example of the use of the present invention. Specifically, the systems, methods, and computer program products of the present invention can be adapted to any number of medical billing systems and medical resources and are not limited to those in anesthesiology practices. For example, the present invention may be used to analyze billing data and develop forecast factors based thereon in a variety of medical practices and/or medical care facilities including, but not limited to: surgical practices, radiology practices, family medicine practices, internal medicine practices, and other medical facilities.

FIG. 1 illustrates an example of a typical conventional network environment 10 in which the systems, methods, and computer program products of the present invention may be employed. The network includes a forecast module 12 (housed in a host computer device, for example). The forecast module 12 is typically connected to a network 14, such as a LAN, WAN, Intranet, or Internet, for example. Also connected to the network are various medical billing systems 11 containing a variety of billing data sets including data that may be indicative of a utilization of at least one medical resource in a selected medical facility during a first time period. For example, data within a billing data set may include, but is not limited to: service case entries corresponding to various services performed during the course of a medical procedure during the first time period (such as a given hour, day, week, month, and/or year, for example). A service case entry may include, in some examples, codes for patient preparation (including the administration of anesthesia, for example), codes for a medical procedure and/or a surgical procedure (such as a surgical procedure performed under general anesthesia), and/or codes for patient recovery (including time spent in a recovery room and/or supervision during recovery by a clinician). The data within the billing data sets may also include, but are not limited to: identification codes for identifying a type of an at least one medical procedure; times of the at least one medical procedure; durations of the at least one medical procedure; locations of the at least one medical facility; personnel identification codes for identifying a clinician performing the at least one medical procedure; payer class (i.e. type of insurance coverage for the medical procedure) and combinations thereof.

Further, as shown in FIG. 1, users may also be connected to the network 14 via personal computers 15 or other types of computing systems. In addition, one or more conversion modules 13 may also be connected to the network 14 such that the forecast module 12 may be capable of interrogating the conversion module 13 so as to be capable of converting the data within the billing data set into a utilization data set comprising utilization information corresponding to a historical demand for the medical resource (such as a procedure room, a clinician, and/or other medical personnel) in at least one medical facility during the first time period.

In operation, the system of the present invention, via the forecast module 12, may provide a web page or other similar electronic form to a user. Using the web page or electronic form, the user may input and/or modify a standard forecast query which may include, for example, a selection of a second time period that may be comparable to the first time period from which the billing data is taken (such as, for example, an upcoming week) or a selection of a particular medical facility (such as a selected anesthesiology and/or operating room suite). Based either on this query, and/or based on a standard query stored in a memory device 22 provided as part of the forecast module 12, the forecast module 12 may, in some embodiments, poll the medical billing systems 11 in order to retrieve one or more billing data sets from the medical billing systems 11 (see step 210 of FIG. 2, for example). According to other embodiments, the retrieval step (see step 210, of FIG. 2, for example) may also comprise a step wherein the medical billing systems 11 periodically "push" medical billing data to the forecast module 12 (as described in further detail below).

Furthermore, the forecast module 12 may also convert data within the billing data set into a utilization data set corresponding to a historical demand for the medical resource in the medical facility during the first time period (see step 220 of FIG. 2, for example). As discussed above, the forecast module 12 may interrogate and/or consult a conversion module 13 so as to be capable of converting the data within the billing data set into a utilization data set comprising utilization information corresponding to a historical demand for the medical resource. In other embodiments, the forecast module 12 may access conversion algorithms and/or a conversion key stored in a memory device 22 that may be provided as part of a computer system hosting the forecasting module 12. For example, medical billing data retrieved from some medical billing systems may not include identifiers for specific types of medical procedures and may instead indicate only a start time and/or duration of a given medical procedure within an anesthesiology practice, for example. In such cases, the forecast module 12 may interrogate one or more of a conversion module 13 and/or a conversion algorithm stored in a memory device 22 in order to convert duration information into, for example, a procedure and/or medical service type. For example, a billed medical procedure having a five minute duration may correlate to a patient preparation step (which may require specific medical resources, such as a registered nurse and a patient prep room). In another example, a billed medical procedure having a one hour duration may correlate to a procedure step (which may require specific medical resources, such as an anesthesiologist and a nurse anesthetist and a sterile procedure room). In yet another example, a billed medical procedure having a different duration may correlate to a post-procedure recovery step (which may require other specific medical resources, such as a registered nurse and a recovery room). In such embodiments, the forecasting module 12 may be capable (by consulting a stored conversion key and/or interrogating a conversion module 13) of converting certain billing data to a standardized format (herein referred to a "utilization data set," for example) that may be better used to generate a forecast factor. According to other examples, the conversion module 13 may house a plurality of different conversion algorithms configured to convert billing data from various different medical billing systems (each of which may generate billing data having a different format) into a standardized "utilization data set" that may be used, in turn, to generate the forecast factor.

Therefore in some system embodiments of the present invention, the forecast module 12 may determine a forecast factor using data within the utilization data set (see, for example, step 230 of FIG. 2). The forecast factor determined by the forecast module 12 may correspond to an expected demand for the medical resource in at least one medical facility during a second time period, wherein the second time period may be subsequent to the first time period, such that the at least one medical resource may be more efficiently utilized and/or scheduled during the second time period (such as an upcoming hour, day, week, month, or year, for example).

According to various system embodiments of the present invention, the forecast module may be capable of accessing a calendar (stored in a memory device 22 for example, and/or accessible via the network 14) such that when determining one or more forecast factors, the forecast module 12 may take into account the holiday calendar is so as to ensure weeks of same type (i.e. "short" holiday weeks) correspond to comparable historical weeks (having stored billing data, for example) before using such stored billing data to forecast demand for a medical resource. For example, time periods with holiday types are matched against equivalent holiday types in the past time periods, non-holiday time periods are matched with non-holiday time periods in past years (not simply by week number, for example). In addition, the forecast module 12 may also be capable of determining a forecast factor wherein selection of the first time period is made such that only full weeks enter the calculations. For example, incomplete weeks at the end of a given time period (such as month's and/or year's end) may be truncated and discarded by the forecast module 12 for the purposes of determining the forecast factor. Such embodiments may provide a more accurate forecast factor so as to more accurately assess demand for medical resources during special event weeks such as Thanksgiving week. The forecast factor determined by the forecast module 12, according to some system embodiments of the present invention, may include, but is not limited to: a percentage of time the at least one medical facility is in use during the first time period; a number of clinicians required to staff the at least one medical procedure; a qualification of a clinician required to staff the at least one medical procedure; a number of concurrent medical procedures occurring in the at least one medical facility during the first time period; and a percentage of time that a selected number of concurrent medical procedures are occurring in the at least one medical facility during the first time period.

The forecast factors generated by the forecast module 12 of the present invention may also include one or more graphical and/or statistical results determined using the retrieved billing data. For example, the forecast factor may comprise a Gantt chart of selected medical procedures in a selected medical facility (such as a selected procedure suite) during a first time period. As shown generally in FIGS. 11-12, the Gantt Chart forecast factor may enable a user to obtain a quick and efficient overview of "busy time of day" and "idle periods" (white areas) in past time periods of interest.

Some forecast factors generated by the system embodiments of the present invention may also comprise financial information obtained from the medical billing systems 11. For example, the forecast module 12 may also be capable of determining a percentage of payer volume (i.e. insurance type volume) within a selected medical facility during a selected first time period. Payers may be defined in a 2-level hierarchy comprising: (1) payer group and (2) payer class (wherein a payer class may comprise one or more payer groups). Each insurance company may pay different amounts for the same procedure. Thus, payer volume forecast factors may allow a user of embodiments of the present system to evaluate how much time was spent doing "well paid work" as opposed to "poorly paid work" in a given medical facility. A payer volume forecast factor may be determined by the forecast module 12 by calculating percentage of volume (wherein volume is herein defined as a number of man-hours (mh)) in each payer class or payer group. Such a forecast factor may also be weighted to emphasize particular payer classes and/or payer groups when calculating the payer volume forecast factor.

According to other system embodiments of the present invention, the forecast module 12 may also be configured to determine a forecast factor that may be indicative of a number of concurrent medical procedures occurring in a medical facility (such as a particular suite of medical procedure rooms). For example, according to one embodiment, demand for a medical resource (such as operating room anesthesia staff) may be accurately predicted. For the purposes of optimizing the forecast factor in one embodiment, an assumption may be made wherein at any given hour (or other selected time unit), one anesthesia nurse staff member is needed to oversee one activity and one anesthesiologist is needed to staff 3-4 concurrent activities. Thus, the concurrent activities forecast factor may be critical to predicting the correct staffing for operating room anesthesia staff. Thus, in some embodiments, the forecast module 12 may determine a concurrent activities forecast factor by determining a number of concurrent medical procedures versus a selected time axis point by day (using, for example, the utilization data set obtained by converting the raw billing data sets retrieved from the medical billing systems 11). According to various system embodiments, the forecast module may then perform a statistical calculation on the number of concurrent medical procedures to determine various forecast factors, including, but not limited to: an average number of concurrent medical procedures occurring in the selected time interval; 50% of the median number of concurrent medical procedures occurring in the selected time interval, maximum number of concurrent medical procedures occurring in the selected time interval, and a distribution of concurrent medical procedures occurring in the selected time interval.

In some other system embodiments, the forecast module may also determine a forecast factor comprising a weekly forecast of concurrent medical procedures per time interval. For example, the forecast module 12 may distribute medical procedures (detected by retrieving the billing data corresponding thereto) into a series of first time periods (using a holiday calendar as described generally above to ensure a comparison of comparable seasonal time periods) and may further utilize a predetermined weighted average (wherein the weighting factors may be stored in a memory device 22) to calculate forecast for a comparable second time period (in the upcoming year, for example). The forecast module 12 may, for example calculate a weighted average forecast factor that gives the most weight to the last year and, may use the following weighting values: 1 year prior: 1.0, 2 years prior: (0.4, 0.6) 3 years prior (0.2, 0.3, 0.5) (wherein the weighting factors are selected depending also on the number of billing data points used to determine the utilization data set).

In some other system embodiments, the forecast module 12 may also calculate a forecast factor comprising a weekly forecast of concurrent medical procedures per time interval using exponential smoothing (such as triple exponential smoothing, for example) statistical techniques. The forecasting factors displayed as a result of such a determination may include, but are not limited to: forecasted values of concurrent medical procedures per time interval for a comparable future week; actual concurrent medical procedures per time interval for the comparable first time period; and forecasted values plus an indication of the error (MAPE) inherent in the forecasted value. According to other system embodiments, the forecast module may also distribute medical procedures into selected first time periods (such as prior months) and use linear regression techniques to calculate forecast factor of volume (in man-minutes, for example) for a second time period (such as a comparable month in the upcoming year). Thus, the forecast module may accurately predict volume in man-minutes, which when determined in line with payer class (as described generally above) may accurately predict revenues for an upcoming time period. Monthly volume can display trends important for quarterly planning, including for example, staff hiring and/or downsizing requirements.

Other system embodiments may comprise a forecast module 12 that may determine a forecast factor that may include, but is not limited to: a maximum number of concurrent medical procedures by time period (such as by week); a correlation between morning and afternoon volume (in man-hours, for example) per time period (i.e. daily); total volume (in man-minutes) per starts (daily or hourly)(which may indicate average duration of medical procedure in minutes); a number of medical procedures started per time period; and a number of medical procedures stopped per time period.

According to various system embodiments of the present invention the forecasting module may comprise a memory device 22 for storing multiple retrieved billing data sets from one or more medical billing systems 11 over the course of a selected number of time periods in order to compile and utilize a wide range of historical billing data over the course of, in some embodiments, several years in order to determine some forecast factors. Thus, the "utilization data set" used by the forecast module to determine a forecast factor may comprise, in some embodiments, stored and/or converted billing data from one or more first time periods that may be comparable to the second time period for which a medical resource demand forecast may be sought.

By converting the billing data to a standardized "utilization data set" to determine the various types of forecast factors described above, the forecast module 12 may be capable of compiling billing data from a number of different medical billing systems 11 within a large health care system, for example, and developing powerful and flexible forecast factors for various administrative levels within the health care system. For example, as described below with respect to step 710 of FIG. 7 (generally depicting a method embodiment of the present invention) some system embodiments of the present invention may further comprise a user interface configured to receive a user input comprising a selection of the forecast factor. Thus, a user may input a selection of one or more medical facilities, medical practices, and/or specific procedure rooms within a large healthcare system. The forecast module may then tailor the compilation of billing data to correlate more closely to the selected forecast factor. For example, if a user selects a forecast factor for a specific operating room suite in a specific hospital, the forecast module may only retrieve billing data corresponding to medical procedures performed in the same and/or comparable operating room suites within the same health care system such that the forecast factor generated using the billing data may be especially reflective of the expected demand for medical resources (including, for example, procedure room space and/or certain types of medical personnel) in the selected operating room suite.

According to some other system embodiments, the forecast module 12 may be further configured to generate the schedule of the at least one medical resource such that the schedule corresponds to the determined forecast factor during the second time period. For example, if the forecast factor indicates that a maximum number of concurrent medical procedures in a four-room surgical suite staffed by three surgeons are occurring during a two-hour block during the middle of the day (see FIG. 9, for example), the forecast module 12 may automatically generate a schedule of clinicians and/or procedure rooms to accommodate the maximum number of concurrent procedures during the middle of the day without scheduling a concurrent maximum number of medical resources during a full shift. In addition, the forecast module 12 may utilize a forecast factor output 810 (see FIG. 8, for example) in order to provide, for example, an overlap of working shifts for one or more medical personnel such that a greater number of medical personnel may be present in the medical facility during the peak hours of concurrent medical procedures (as indicated by the forecast factor determined by analyzing billing data from a previous comparable time period). In addition, the forecast module 12 may also schedule a maximum number of procedure rooms (for example 4 procedure rooms) using the forecast factor output 920 of FIG. 9 (which shows pie chart 920 graphs of the percentage of time during a particular hour that a given number of concurrent procedures were occurring during a comparable time period) only during the portion of a particular time period that multiple concurrent procedures are performed (as indicated by the billing data). According to further embodiments, the forecast module 12 may also transfer the generated schedule of medical resources to a scheduling calendar. For example, the forecast module 12 may transfer the generated schedule to a computer device 15 via the network 14 such that the user may view and/or manually edit the generated schedule generated by the forecast module 12 in an electronic calendar program and/or scheduling module.

As shown generally in FIGS. 8-12, the forecast module 12 may also generate a display 800 of the forecast factor. Some system embodiments of the present invention may comprise a user interface (such as a display 24 provided as a component of the forecast module 12 and/or a computer device 15 in communication with the forecast module 12 via the network 14. According to some embodiments, the forecast module 12 may display the forecast factor to the user via said user interface in a display 800 that may include, but is not limited to: a chart of substantially concurrent medical procedures in the at least one medical facility during the first time period (see, for example, FIGS. 9-12, generally showing pie charts of the percentage of time that different numbers of concurrent medical procedures were billed for a first time period); a chart of a quantity of the at least one medical procedure in the at least one medical facility during the first time period; and a Gantt chart of the at least one medical procedure during the first time period (see FIGS. 11-12, showing Gantt charts of two different workdays (Tuesday and Friday) within a given first time period (a week)).

FIG. 8 shows a display 800 generated by one forecast module 12 embodiment of the present invention, wherein the display 800 includes a forecast factor plot comprising a plot of a billed medical resource (in this case, a number of medical personnel) versus time of day for a particular Monday (as indicated by the data point legend 840 that may be displayed as part of the display 800). Thus, in some system embodiments, the forecast module 12 may be capable of displaying billed medical personnel versus time of day for a plurality of days within a selected time period concurrently in a single display 800 by utilizing different data point indicator shapes as shown, for example, in the data point legend 840). According to various system embodiments of the present invention, the forecast module 12 may use billing data retrieved from the billing data systems 11 to determine a number of medical personnel (including, in some instances a type of medical personnel (such as a certified nurse anesthetist, and/or an anesthesiologist) whose time may have been billed during a prior Monday of a comparable week (i.e. a non-holiday Monday in the middle of the summer) and determine a forecast factor (i.e. that no more than 10 medical personnel should be scheduled before 0730 or after 1200 on such a Monday) that may be shown in a display 800 as shown in FIG. 8. The plotted forecast factor 810 of FIG. 8 may also generally indicate that a scheduling administrator should not schedule 13 medical personnel to work a ten-hour shift from 0700-1700 when the peak demand for this medical resource (13 medical personnel, for example) only exists on comparable Mondays for approximately 2 hours (0930-1130).

Various system embodiments of the present invention also provide a forecast module 12 that may be capable of generating a display 800 of a chart of substantially concurrent medical procedures in the at least one medical facility during the first time period (such as a given workday). For example, FIGS. 9 and 10 illustrate a display 800 that may be generated by the forecast module 12 of the present invention to indicate the percentage of time within a selected time period that a specific number of concurrent medical procedures are typically running (as ascertained by the forecast module 12 using billing data retrieved from the medical billing systems 11, for example). In the example depicted in FIGS. 9 and 10, a particular medical facility (such as an anesthesiology department within a hospital) has a multiple-year history of scheduling four procedure rooms for a three-surgeon medical team for the weekdays Tuesday, Wednesday, Thursday, and Friday. FIG. 9 shows, for example, a group of pie charts 920 (for each hour of a Tuesday) showing the percentage of time within a specific hour 910, that a number of concurrent medical procedures may be occurring within a given medical facility (such as a suite of four procedure rooms). A pie chart 920 corresponding to 1300, Tuesday, indicates (using the concurrent procedure tags 930) that: 4 procedures were taking place concurrently for 15 percent of the hour between 1300 and 1400, 3 procedures were taking place concurrently for 23 percent of the hour between 1300 and 1400, 2 procedures were taking place concurrently for 15 percent of the hour between 1300 and 1400, 1 procedure was taking place for 23 percent of the hour between 1300 and 1400, and no procedures were taking place for 23 percent of the hour between 1300 and 1400. As described below with respect to FIG. 7, some system, method, and computer program embodiments of the present invention may allow a user to select the forecast factor that may be determined and displayed (via the display 800) by the forecast module 12. Thus, a user may select to plot a forecast factor (such as a concurrent procedures pie chart 920 for selected medical resources (i.e. the three-surgeon team, using a 4-room procedure suite, as described above), over the course of a selected time period (i.e. a Tuesday) which would lead to a forecast factor plot as shown generally in FIG. 9. Alternatively, as shown in FIG. 10, the forecast module 12 may also be capable of determining and/or plotting (in a display 800, for example) a forecast factor of concurrent medical procedures for the three-surgeon team described above for a Friday. As shown in FIG. 10, for example, the pie chart 930 corresponding to the 1200 hour 910 indicates that only one procedure was performed (for only 19 percent of the plotted hour (as indicated by the concurrent procedure tag 930 in the display 800)). Thus, the display 800 generated by the forecast module 12 may allow a user (such as a scheduling administrator and/or clinician) to quickly identify medical resource scheduling inefficiencies by scanning the displays 800 for long periods of time having 2 or less concurrent procedures running. For example, the display 800 shown in FIG. 10 may indicate that for Fridays (during a comparable season to the Friday forecast factor plotted in FIG. 10), the three-surgeon team may only require, at most, three procedure rooms (for a two hour block of time) and/or that one of the team members may take a shortened Friday work schedule.

FIGS. 11-12 show an alternate Gantt-type forecast factor display 800 that may be generated by the forecast module 12 of the present invention according to some system embodiments of the present invention. For example, as shown in FIG. 11 Gantt chart display 800 may be generated to plot medical procedures (by individual billed case number 1120, for example) versus time 1130 for a selected historical first time period that may be comparable (i.e. a non-holiday, midsummer week) to an upcoming second time period. The Gantt chart display 800 may depict the duration 1140 of individual procedures and show how concurrent medical procedures have lined up during the course of a typical Tuesday (FIG. 11, for example, corresponds to the display of pie charts 930 shown generally in FIG. 9). FIG. 12 shows a Gantt chart display 800 showing medical procedures being performed by the three-surgeon team on a typical Friday (corresponding to the pie chart 930 display 800 of FIG. 10, for example). As FIG. 12 indicates, the forecast factor generated by the forecast module 12 indicates that there may be little need for multiple procedure rooms (or medical staff schedule overlap) on a typical Friday (at least as indicated by a previous comparable Friday's billing data and/or a weighted average thereof based on historical data from multiple comparable time periods).

As described generally above, some system embodiments of the present invention may also comprise one or more user interfaces for displaying the forecast factor to a user. For example, the user interface may comprise a computer device 15 in communication with the forecast module 12 via the network 14. In other embodiments, the user interface may comprise a display 24 and/or keyboard interface 26 that may be included as part of a computer device that may host the forecast module 12 of the present invention. In any case, the user interface may also be configured to receive a user input comprising a selection of the forecast factor. For example, as shown generally in FIG. 13, the user interface may be capable of generating a display 800 including one or more input areas 1310-1390 such that a user may input a query and/or a specific selection of a forecast factor that they would like the forecast module to determine based upon the billing data retrieved from one or more medical billing systems 11. For example, as shown in FIG. 13, the selection display 800 may comprise drop down menus 1310-1330 for selecting a forecast factor based upon certain utilization data criteria which may include, but are not limited to: a medical procedure/activity type 1310, a medical resource (staff) type 1320, and an other staff type 1330 (i.e. non-medical and/or administrative staff). In other embodiments (see FIG. 13, for example) the selection display 800 may also comprise text boxes wherein a user may input other selection criteria for modifying the parameters of the forecast factor determined by the forecast module. For example, the selection display 800 may comprise various text boxes 1330-1390 wherein a user may input forecast factor criteria including, but not limited to: a medical staff number in include in the forecast factor determination 1340, a medical staff number to exclude from the forecast factor determination 1350; a payer class (insurance company, for example) 1360, a payer class to exclude from the forecast factor determination 1370; a location code (corresponding to a selected medical facility, for example) 1380; a location code to exclude from the forecast factor determination 1390; a procedure code (corresponding to a medical procedure type to be included in the forecast factor determination. Thus, as shown generally in FIG. 13, some system embodiments of the present invention may allow the user to selectively modify the parameters of the forecast factor determination in order to change the focus of the forecast factor determination as performed by the forecast module. For example, a user may choose to focus on scheduling profitable medical procedures by selecting a forecast factor that includes profitable payer classes. The user may also choose to exclude certain staff identification numbers (for staff members with scheduled vacations during the upcoming second time period (for which the forecast factor and/or schedule is being developed)).

As illustrated in exploded portion of FIG. 1 corresponding to the forecast module 12, the forecast module 12 of the system embodiments of the present invention may be generally embodied as a typical computer, server or mainframe system depending on the embodiment. The host computer 12 may generally include a processing element 20, such as a microprocessor, VLSI, ASIC, etc., a storage device 22, display 24, keyboard and mouse interface 26, and a network interface 28.

In some embodiments, the host computer system 12 may poll one or more medical billing systems 11 for medical billing data each time a user requests a particular forecast factor (via a personal computer 15, for example). However, in some embodiments, such frequent requests may slow down and/or disrupt the medical billing system 11. Further, accessing the medical billing system 11 may have an associated processing delay. For this reason, in some embodiments, the forecast module 12 may further include a prepopulated cache 30 from which medical billing data (and corresponding medical resource usage data) is derived for providing forecast factors according to various embodiments of the present invention. Specifically, as shown in FIG. 1, the forecast module 12 of the present invention includes an availability cache 30 located in the storage device 22. The availability cache 30 is populated with medical billing data from a first time period that may be required for determining a forecast factor for an expected demand for a medical resource during a comparable subsequent second time period. In such embodiments, the data retrieved from the availability cache 30 may also be used to determine a forecast factor and/or reschedule a medical resource using the forecast factor, as described above, and be presented to a user's personal computer 15 (or other user interface) in a display.

Furthermore, according to various system embodiments of the present invention, it should be understood that medical billing data may be transferred from one or more medical billing systems 11 to the forecast module 12 (or a memory device 22 in communication therewith) via "push" and/or "pull" techniques. For example, according to "pull" techniques, one skilled in the art will appreciate that the forecast module 12 may periodically (in response to a user input, and/or at a predetermined interval, for example) interrogate one or more medical billing systems 11 to "pull" medical billing data sets therefrom. Furthermore, according to other system embodiments, "push" techniques may be used, wherein one or more medical billing systems 11 may be adapted to periodically (monthly, weekly, and/or daily, for example) "push" medical billing data to the forecast module 12 (via a network 14 connection, for example) and/or to the storage device 22 that may be included as a component of the forecast module 12 of the present invention. Thus, as described above, either of the described "pull" or "push" techniques may also be used to populate an availability cache 30 provided as part of the memory device 22 of the forecast module 12. As one skilled in the art will appreciate, similar "push" and/or "pull" techniques may also be used to transfer descriptive and/or conversion data from one or more conversion modules 13 to the forecast module 12 (via a network 14, for example) to aid the forecast module in converting raw medical billing data into a usable forecast factor that may be displayed to a user.

The various operations of the present invention may be performed either by hardware in the form of ASIC chips or other specialized hardware or by operation of software ran by a processing element. In the latter case, the storage device 22 may also further include the various computer software programs and modules used to implement the operations of the present invention.

FIG. 2 is a generalized illustration of the operations performed by the systems, methods, and computer program products of the present invention to generate the various forecast factors discussed above and to generate the various forecast factor displays illustrated in FIGS. 2-7. The description of this operation is given by example to the system schematic shown generally in FIG. 1, and to the various display illustrations shown in FIGS. 8-13.

FIG. 2 shows a method for optimizing a schedule of at least one medical resource (such as, for example, a clinician and/or a medical procedure room) in at least one medical facility using a billing data set retrieved from a medical billing system 11. As described generally above with respect to the various system embodiments of the present invention, the billing data set may corresponding to at least one medical procedure being performed using the at least one medical resource in the at least one medical facility during a first time period (such as a comparable past week and/or a statistical compilation of billing data from a plurality of comparable past weeks). In addition, the data within the billing data set may also be indicative of a utilization of the at least one medical resource during the first time period. As discussed above, data within the billing data set may include, but is not limited to: an identification code for identifying a type of the at least one medical procedure; a time of the at least one medical procedure; a duration of the at least one medical procedure; a location of the at least one medical facility; a personnel identification code for identifying a clinician performing the at least one medical procedure; and/or combinations thereof.

As shown generally in FIG. 2, some method embodiments may comprise step 210 for retrieving the billing data set from the medical billing system 11, and step 220 for converting data within the billing data set into a utilization data set corresponding to a historical demand for the medical resource in the at least one medical facility during the first time period. Finally, the various method embodiments of the present invention may also comprise step 230 for determining a forecast factor using data within the utilization data set. The forecast factor may correspond, for example, to an expected demand for the medical resource in the at least one medical facility during a second time period, the second time period being subsequent to the first time period, such that the at least one medical resource may be efficiently utilized during the second time period.

As described generally above, step 230 may comprise performing a number of different statistical calculations on the utilization data set for determining the forecast factor. For example, step 230 may include, but is not limited to: generating a Gantt chart of medical procedures billed during the first time period; calculating an average number of concurrent medical procedures during a time interval within the first time period; calculating a percentage of payer volume; calculating forecasts of concurrent medical procedures during a time interval within the first time period using statistical techniques such as concurrent weighted averages, exponential smoothing (such as triple exponential smoothing, for example), and linear regression; and calculating an average number of medical procedure starts and stops during the first time period. According to other method embodiments, the forecast factor generated in step 230 may include, but is not limited to: a percentage of time the at least one medical facility is in use during the first time period; a number of clinicians required to staff the at least one medical procedure; a qualification of a clinician required to staff the at least one medical procedure; a number of concurrent medical procedures occurring in the at least one medical facility during the first time period; and a percentage of time that a selected number of concurrent medical procedures are occurring in the at least one medical facility during the first time period.

As shown in FIG. 3, some method embodiments of the present invention may also comprise step 310 for generating and/or redistributing the schedule of the at least one medical resource such that the schedule corresponds to the determined forecast factor during the second time period. Thus, in some method embodiments, step 310 may comprise generating and/or redistributing a schedule of a medical resource (such as reserved procedure rooms and/or the schedules of physicians and/or other clinical staff) such that the schedule better aligns with the forecast factor (which is calculated, at least in part, using historical utilization data (see step 230) that is based, in turn, upon actual billing data for a first time period that may be directly comparable to the second time period (i.e. an upcoming day, week, month, and/or year for which a schedule is to be developed). For example, and as discussed generally above with respect to FIG. 9, if the forecast factor indicates that a maximum number of concurrent medical procedures in a four-room surgical suite staffed by three surgeons are occurring during a two-hour block during the middle of the day (see FIG. 9, for example), the forecast module 12 may automatically generate and/or redistribute a schedule of clinicians and/or procedure rooms to accommodate the maximum number of concurrent procedures during the middle of the day without scheduling a concurrent maximum number of medical resources during a full shift.

Furthermore, in some method embodiments (as shown in FIG. 4), the method may further comprise step 410 for transferring the generated and/or redistributed schedule of medical resources to a scheduling calendar. For example, as described above with respect to the various system embodiments of the present invention, the forecast module 12 may transfer the schedule to a computer device 15 via the network 14 such that the user may view and/or manually edit the schedule generated by the forecast module 12 in an electronic calendar program and/or scheduling module.

FIG. 5 shows another method embodiment of the present invention further comprising step 510 for displaying the forecast factor (determined in step 230, for example) to a user. As discussed above with respect to the system embodiments of the present invention, the forecast module 12 may, for example, generate a graphical depiction of a forecast factor in a display 800 (see FIGS. 8-12) such that a user may view a graphical depiction of the forecast of a projected demand for a specific medical resource during an upcoming second time period (that may be comparable to a first time period from which actual billing data may be retrieved (see step 210) and based upon which medical resource utilization data 220 is generated. As described in further detail above with respect to various system embodiments of the present invention, the displaying step 510 may also further comprise displaying the forecast factor to the user in a graphical display 800 (see FIGS. 8-12, for example) that may include, but is not limited to: a chart of substantially concurrent medical procedures in the at least one medical facility during the first time period (see the percentage of concurrent medical procedures pie charts of FIGS. 9 and 10 (depicting concurrent medical procedures for a Tuesday and Friday, respectively); a chart of a quantity of the at least one medical procedure in the at least one medical facility during the first time period (see for example, FIG. 8, generally depicting a volume (in man hours) of a medical resource (corresponding generally to a number of medical procedures) during a particular Tuesday); and a Gantt chart of the at least one medical procedure during the first time period (see generally, FIGS. 11 and 12, showing Gantt charts of medical procedures in a particular medical treatment suite during a typical Tuesday and Friday, respectively).

According to other method embodiments, the display step 510 may also comprise generating a text and/or numerical display of one or more forecast factors that may be generated according to step 230 in various method embodiments of the present invention. For example, the forecast factor displayed to the user as part of step 510 may comprise a numerical indication of a forecast medical procedure volume (in man hours, for a selected second time period corresponding to a first time period for which billing data indicating medical procedure volume may be available).

FIG. 6 shows another alternate method embodiment of the present invention comprise step 610 for interrogating a conversion module 13 (which may be in communication with a forecast module 12 via a computer network 14) prior to step 220 for converting data within the retrieved billing data set (see step 210) into a utilization data set that may be indicative of historical demand for a given medical resource at a selected medical facility during a first time period (which may be comparable to a second time period for which a medical resource schedule is yet to be developed). The interrogating step 610 may comprise, in some method embodiments, interrogating a conversion module 13 (see FIG. 1) comprising data and corresponding utilization information so as to convert the data within the billing data set into a utilization data set comprising the utilization information corresponding to a historical demand for the at least one medical resource in the at least one medical facility during the first time period. As discussed above with respect to the various system embodiments of the present invention, the forecast module 12 may interrogate a conversion module 13 so as to be capable of converting the data within the billing data set into a utilization data set comprising utilization information corresponding to a historical demand for the medical resource. In other embodiments, the forecast module 12 may access conversion data and/or a conversion key stored in a memory device 22 that may be provided as part of a computer system hosting the forecasting module 12. For example, medical billing data retrieved from some medical billing systems may not include identifiers for specific types of medical procedures and may instead indicate only a start time and/or duration of a given medical procedure within an anesthesiology practice. In such cases, the forecast module 12 may interrogate one or more of a conversion module 13 and/or a conversion key stored in a memory device 22 in order to convert duration information into, for example, a procedure and/or medical service type.

Finally, as shown in FIG. 7, some method embodiments of the present invention may also comprise step 710 for receiving a user input comprising a selection of the forecast factor. For example, as shown generally in FIG. 13, various embodiments of the present invention may generate a user input display 800 for receiving a user input that may comprise one or more selections for tailoring one or more parameters of the forecast factor to a specific information requirement of the user. For example, as shown in FIG. 13, the user may in some embodiments, input a selection of various forecast factor parameters prior to the performance of steps 210-230 for determining a forecast factor. Such input parameters may include, but are not limited to: a medical procedure/activity type 1310; a medical resource (staff) type 1320; general staff type 1330 (i.e. non-medical and/or administrative staff); a medical staff number in include in the forecast factor determination 1340; a medical staff number to exclude from the forecast factor determination 1350; a payer class (insurance company, for example) 1360; a payer class to exclude from the forecast factor determination 1370; a location code (corresponding to a selected medical facility, for example) 1380; a location code to exclude from the forecast factor determination 1390; a procedure code (corresponding to a medical procedure type to be included in the forecast factor determination. Thus, as shown generally in FIG. 13, some method embodiments of the present invention may allow the user to selectively modify the parameters of the forecast factor determination in order to change the focus of the forecast factor determination of step 230.

In addition to providing apparatus and methods, the present invention also provides computer program products for performing the operations described above. The computer program products have a computer readable storage medium having computer readable program code means embodied in the medium. With reference to FIG. 1, the computer readable storage medium may be part of the storage device 22, not shown, and may implement the computer readable program code means to perform the above discussed operations.

In this regard, FIGS. 2-7 are block diagram illustrations of methods, systems and program products according to the invention. It will be understood that each block or step of the block diagram and combinations of blocks in the block diagram can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for optimizing a schedule of at least one medical resource in at least one medical facility using a billing data set, the system comprising:

a medical billing system comprising the billing data corresponding to at least one medical procedure being performed using the at least one medical resource in the at least one medical facility during a first time period, the data within the billing data set being indicative of a utilization of the at least one medical resource during the first time period; and a forecasting module in communication with said medical billing system, wherein said forecasting module:
retrieves the billing data set from the medical billing system;
converts data within the billing data set into a utilization data set corresponding to a historical demand for the at least one medical resource in the at least one medical facility during the first time period;
determines a forecast factor using data within the utilization data set, the forecast factor corresponding to an expected demand for the at least one medical resource in the at least one medical facility during a second time period, the second time period being subsequent to the first time period; and generates a schedule for the at least one medical resource based on the determined forecast factor indicating at least a date and time during the second time period when the at least one medical resource is expected to be utilized.

2. A system according to claim 1, wherein said forecasting module transfers the generated schedule to a scheduling calendar.

3. A system according to claim 1, wherein said forecasting module comprises a memory device for storing the retrieved billing data set.

4. A system according to claim 1, further comprising a user interface for displaying the forecast factor to a user.

5. A system according to claim 4, wherein said user interface is configured to receive a user input comprising a selection of the forecast factor.

6. A system according to claim 4, wherein said forecast module displays the forecast factor to the user via said user interface in at least one of:
a chart of substantially concurrent medical procedures in the at least one medical facility during the first time period;
a chart of a quantity of the at least one medical procedure in the at least one medical facility during the first time period; and
a Gantt chart of the at least one medical procedure during the first time period.

7. A system according to claim 1, wherein the data within the billing data set comprises at least one of:
an identification code for identifying a type of the at least one medical procedure;
a time of the at least one medical procedure;
a duration of the at least one medical procedure;
a location of the at least one medical facility;
a personnel identification code for identifying a clinician performing the at least one medical procedure; and
combinations thereof.

8. A system according to claim 1, wherein the forecast factor comprises at least one of:
a percentage of time the at least one medical facility is in use during the first time period;
a number of clinicians required to staff the at least one medical procedure;
a qualification of a clinician required to staff the at least one medical procedure;
a number of concurrent medical procedures occurring in the at least one medical facility during the first time period;
and a percentage of time that a selected number of concurrent medical procedures are occurring in the at least one medical facility during the first time period.

9. A system according to claim 1 wherein the first and second time periods are comparable time periods of substantially equivalent duration comprising at least one of:
a day;
a week;
a month; and
a year.

10. A system according to claim 1, further comprising a conversion module comprising data and corresponding utilization information, and wherein said forecasting module interrogates said conversion module so as to convert the data within the billing data set into a utilization data set comprising the utilization information corresponding to a historical demand for the at least one medical resource in the at least one medical facility during the first time period.

11. A system according to claim 1, wherein the at least one medical resource is at least one of:
a clinician; and
a medical procedure room within the at least one medical facility.

12. A system according to claim 1,
wherein the at least one medical resource comprises a plurality of like medical resources each being interchangeable with one another such that a first of the plurality functions similarly to a second of the plurality;
wherein the forecast factor corresponds to an expected demand for the plurality of like medical resources, the forecast factor comprising a number of concurrent medical procedures occurring in the at least one medical facility during the first time period; and
wherein the forecast factor is configured such that the plurality of like medical resources can be scheduled for efficient utilization of each of the plurality during the second time period.

13. A system according to claim 12, wherein said forecasting module generates the schedule of the at least one medical resource such that the schedule corresponds to the determined forecast factor during the second time period, the plurality of like medical resources each being scheduled for efficient utilization of each of the plurality during the second time period.

14. A system according to claim 1, wherein the forecasting module generates the schedule for the at least one medical resource based on the determined forecast factor indicating at least a date and time, the time comprising a time interval, during the second time period when the at least one medical resource is expected to be utilized.

15. A system according to claim 1, wherein the forecasting module generates the schedule for the at least one medical resource based on the determined forecast factor indicating at least a date and time, the date comprising a date range, during the second time period when the at least one medical resource is expected to be utilized.

16. A method for optimizing a schedule of at least one medical resource in at least one medical facility using a billing data set from a medical billing system, the billing data set corresponding to at least one medical procedure being performed using the at least one medical resource in the at least one medical facility during a first time period, the data within the billing data set being indicative of a utilization of the at least one medical resource during the first time period, the method comprising:
retrieving the billing data set from the medical billing system using a processing element;
converting data within the billing data set into a utilization data set corresponding to a historical demand for the at least one medical resource in the at least one medical facility during the first time period using a processing element;
determining a forecast factor using data within the utilization data set, the forecast factor corresponding to an expected demand for the at least one medical resource in the at least one medical facility during a second time period, the second time period being subsequent to the first time period using a processing element; and
generating a schedule for the at least one medical resource based on the determined forecast factor indicating at least a date and time during the second time period when the at least one medical resource is expected to be utilized using a processing element.

17. A method according to claim 16, further comprising receiving a user input comprising a selection of the forecast factor.

18. A method according to claim 16, further comprising transferring the generated schedule to a scheduling calendar.

19. A method according to claim 16, further comprising displaying the forecast factor to a user.

20. A method according to claim 19, wherein the displaying step further comprises displaying the forecast factor to the user in at least one of:
- a chart of substantially concurrent medical procedures in the at least one medical facility during the first time period;
- a chart of a quantity of the at least one medical procedure in the at least one medical facility during the first time period; and
- a Gantt chart of the at least one medical procedure during the first time period.

21. A method according to claim 16, wherein the data within the billing data set comprises at least one of:
- an identification code for identifying a type of the at least one medical procedure;
- a time of the at least one medical procedure;
- a duration of the at least one medical procedure; a location of the at least one medical facility;
- a personnel identification code for identifying a clinician performing the at least one medical procedure;
- and combinations thereof.

22. A method according to claim 16, wherein the forecast factor comprises at least one of:
- a percentage of time the at least one medical facility is in use during the first time period;
- a number of clinicians required to staff the at least one medical procedure;
- a qualification of a clinician required to staff the at least one medical procedure;
- a number of concurrent medical procedures occurring in the at least one medical facility during the first time period; and
- a percentage of time that a selected number of concurrent medical procedures are occurring in the at least one medical facility during the first time period.

23. A method according to claim 16 wherein the first and second time periods are comparable time periods of substantially equivalent duration comprising at least one of
- a day;
- a week;
- a month; and
- a year.

24. A method according to claim 16, further comprising interrogating a conversion module comprising data and corresponding utilization information so as to convert the data within the billing data set into a utilization data set comprising the utilization information corresponding to a historical demand for the at least one medical resource in the at least one medical facility during the first time period.

25. A method according to claim 16, wherein the at least one medical resource is at least one of:
- a clinician; and
- a medical procedure room within the at least one medical facility.

26. A method according to claim 16,
wherein the at least one medical resource comprises a plurality of like medical resources each being interchangeable with one another such that a first of the plurality functions similarly to a second of the plurality;
wherein the forecast factor corresponds to an expected demand for the plurality of like medical resources, the forecast factor comprising a number of concurrent medical procedures occurring in the at least one medical facility during the first time period; and
wherein the forecast factor is configured such that the plurality of like medical resources can be scheduled for efficient utilization of each of the plurality during the second time period.

27. A method according to claim 26, wherein said generating a schedule comprises generating the schedule for the at least one medical resource such that the schedule corresponds to the determined forecast factor during the second time period, the plurality of like medical resources each being scheduled for efficient utilization of each of the plurality during the second time period.

28. A method according to claim 16, wherein generating the schedule comprises generating the schedule for the at least one medical resource based on the determined forecast factor indicating at least a date and time, the time comprising a time interval, during the second time period when the at least one medical resource is expected to be utilized.

29. A method according to claim 16, wherein generating the schedule comprises generating the schedule for the at least one medical resource based on the determined forecast factor indicating at least a date and time, the date comprising a date range, during the second time period when the at least one medical resource is expected to be utilized.

30. A computer program product for optimizing a schedule of at least one medical resource in at least one medical facility by retrieving a billing data set from a medical billing system, the billing data set corresponding to at least one medical procedure being performed using the at least one medical resource in the at least one medical facility during a first time period, the data within the billing data set being indicative of a utilization of the at least one medical resource during the first time period, the computer program product comprising a non-transitory computer-readable storage medium having computer-readable program code instructions stored therein comprising:
- first computer instruction means for retrieving the billing data set from the medical billing system;
- second computer instruction means for converting data within the billing data set into a utilization data set corresponding to a historical demand for the at least one medical resource in the at least one medical facility during the first time period;
- third computer instruction means for determining a forecast factor using data within the utilization data set, the forecast factor corresponding to an expected demand for the at least one medical resource in the at least one medical facility during a second time period, the second time period being subsequent to the first time period; and
- fourth computer instruction means for generating a schedule for the at least one medical resource based on the determined forecast factor indicating at least a date and time during the second time period when the at least one medical resource is expected to be utilized using processing element.

31. A computer program product according to claim 30, further comprising fifth computer instruction means for receiving a user input comprising a selection of the forecast factor.

32. A computer program product according to claim 30, further comprising sixth computer instruction means for transferring the generated schedule to a scheduling calendar.

33. A computer program product according to claim 30, further comprising seventh computer instruction means for displaying the forecast factor to a user.

34. A computer program product according to claim 33, wherein the seventh computer instruction means for displaying further comprises ninth computer instruction means for displaying the forecast factor to the user in at least one of:
- a chart of substantially concurrent medical procedures in the at least one medical facility during the first time period;
- a chart of a quantity of the at least one medical procedure in the at least one medical facility during the first time period; and
- a Gantt chart of the at least one medical procedure during the first time period.

35. A computer program product according to claim 30, wherein the data within the billing data set comprises at least one of:
- an identification code for identifying a type of the at least one medical procedure;
- a time of the at least one medical procedure;
- a duration of the at least one medical procedure; a location of the at least one medical facility;
- a personnel identification code for identifying a clinician performing the at least one medical procedure; and combinations thereof.

36. A computer program product according to claim 30, wherein the forecast factor comprises at least one of a percentage of time the at least one medical facility is in use during the first time period;
- a number of clinicians required to staff the at least one medical procedure;
- a qualification of a clinician required to staff the at least one medical procedure;
- a number of concurrent medical procedures occurring in the at least one medical facility during the first time period; and
- a percentage of time that a selected number of concurrent medical procedures are occurring in the at least one medical facility during the first time period.

37. A computer program product according to claim 30 wherein the first and second time periods are comparable time periods of substantially equivalent duration comprising at least one of
- a day;
- a week;
- a month; and
- a year.

38. A computer program product according to claim 30, further comprising eighth computer instruction means for interrogating a conversion module comprising data and corresponding utilization information so as to convert the data within the billing data set into a utilization data set comprising the utilization information corresponding to a historical demand for the at least one medical resource in the at least one medical facility during the first time period.

39. A computer program product according to claim 30, wherein the at least one medical resource is at least one of:
- a clinician; and
- a medical procedure room within the at least one medical facility.

40. A computer program product according to claim 30,
- wherein the at least one medical resource comprises a plurality of like medical resources each being interchangeable with one another such that a first of the plurality functions similarly to a second of the plurality;
- wherein the forecast factor corresponds to an expected demand for the plurality of like medical resources, the forecast factor comprising a number of concurrent medical procedures occurring in the at least one medical facility during the first time period; and
- wherein the forecast factor is configured such that the plurality of like medical resources can be scheduled for efficient utilization of each of the plurality during the second time period.

41. A computer program product according to claim 40, wherein said fourth computer instruction means for generating a schedule comprise computer instruction means for generating the schedule of the at least one medical resource such that the schedule corresponds to the determined forecast factor during the second time period, the plurality of like medical resources each being scheduled for efficient utilization of each of the plurality during the second time period.

42. A computer program product according to claim 30, wherein the fourth computer instruction means for generating a schedule comprise computer instruction means for generating the schedule for the at least one medical resource based on the determined forecast factor indicating at least a date and time, the time comprising a time interval, during the second time period when the at least one medical resource is expected to be utilized.

43. A computer program product according to claim 30, wherein the fourth computer instruction means for generating a schedule comprise computer instruction means for generating the schedule for the at least one medical resource based on the determined forecast factor indicating at least a date and time, the date comprising a date range, during the second time period when the at least one medical resource is expected to be utilized.

* * * * *